(12) United States Patent
Bantick et al.

(10) Patent No.: US 6,770,646 B2
(45) Date of Patent: Aug. 3, 2004

(54) SUBSTITUTED FUSED PYRIDAZINONE COMPOUNDS; COMPOSITION AND USE THEREOF

(75) Inventors: John Bantick, Burton-on-the-Wolds (GB); Martin Cooper, Loughborough (GB); Philip Thorne, Loughborough (GB); Matthew Perry, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 78 days.

(21) Appl. No.: 10/006,244

(22) Filed: Dec. 10, 2001

(65) Prior Publication Data

US 2002/0099055 A1 Jul. 25, 2002

Related U.S. Application Data

(62) Division of application No. 09/214,755, filed on Jan. 12, 1999, now Pat. No. 6,342,601.

(30) Foreign Application Priority Data

| Dec. 5, 1997 | (SE) | ............................................... 9704542 |
| Jun. 4, 1998 | (SE) | ............................................... 9801989 |
| Dec. 1, 1998 | (WO) | ............................... PCT/SE98/02191 |

(51) Int. Cl.$^7$ ..................... A61K 31/50; C07D 487/00
(52) U.S. Cl. ...................................... 514/248; 544/235
(58) Field of Search .......................... 514/248; 544/235

(56) References Cited

U.S. PATENT DOCUMENTS 5,753,664 A * 5/1998 Aono et al. ............... 514/259.4

FOREIGN PATENT DOCUMENTS

| EP | 0 475 527 A2 | 3/1992 |
| EP | 0 534 443 A1 | 3/1993 |
| FR | 1453897 | 8/1966 |
| FR | 2 478 640 | 9/1981 |
| WO | 91/12251 | 8/1991 |

OTHER PUBLICATIONS

Chemical Abstracts, 28–Heterocycles, vol. 115, pp. 869 (1991).
Chemical Abstracts, Accession No. 115:256193, Ohi et al, 1991.
Yamaguchi et al, "Novel Antiasthmatic Agents with Dual . . . ," Chem. Pharm. Bull., vol. 43, No. 2, pp. 236–240 (1995).
Bulletin De La Societe Chimique De France, vol. 11, 1967; par Max Robba et al; "No. 727. –Contribution à l' étude de la thiéno–[2,3–d] pyridazine et de la thiéno–[3,4–d] pyridazine ("")"; pp. 4220–4235, p. 4220, Nos. 14, 15; p. 4221, Nos. 19, 10; p. 4223, Nos. 10,46, 40,15.
STN International, File CAPLUS, CAPLUS accession No. 1995:932946, Yutilov, Yu. M. et al; "Reaction of 7–nitrothieno(3,2–c)pyridine–4–one with hydrazine", Zh. Org. Khim. (1995), 31(2), 304.
Heterocycles; vol. 40, No. 1, 1995, Francisco Farina et al.; "1,3–Dipolar Cycloadditions of an Aziridine via Azomethine Ylide to 2–Methylpyridazin–3(2H)–Ones"; pp. 379–386.
Tetrahedron, vol. 40, No. 20, 1984, Sermin Inel, "Pyrrole Studies: 31.1 The Structures of Potentially Tautomeric 1,2–Dihydro–6H–Pyrrolo(3,4–d)Pyridazine–1–Ones and 1,2,3,4–Tetrahydro–6H–Pyrrolo(3,4–d)Pyridazine–1,4–Diones", pp. 3979–3986, p. 3981, Nos. 10 a,b,c,d,e; p. 3980 Nos. 2a,b,c,d,e.
Société Chimiquede France Paris Bulletin; vol. 7, 1967, par Max Robba et al, "No. 447. –Syntése de thiéno–(2,3–d)pyridazines et de thiéno–(3,4–d) pyridazines à partir de dérivés thiophéniques"; pp. 2495–2507, p. 2499, Nos. 46–48, 61–65.

* cited by examiner

Primary Examiner—Mukund J. Shah
Assistant Examiner—Tamthom N. Truong
(74) Attorney, Agent, or Firm—Nixon & Vanderhye

(57) ABSTRACT

The invention provides certain pyrrolo-, thieno-, furano-and pyrazolo-[3,4-d]-pyridazinones, processes for their preparation, pharmaceutical compositions containing them, a process for preparing the pharmaceutical compositions, and methods of treatment involving their use.

13 Claims, No Drawings

SUBSTITUTED FUSED PYRIDAZINONE COMPOUNDS; COMPOSITION AND USE THEREOF

This application is a division of application Ser. No. 09/214,755, filed Jan. 12, 1999, now U.S. Pat. No. 6,342,601, the entire content of which is hereby incorporated by reference in this application.

The present invention relates to certain pyrrolo-, thieno-, furano-and pyrazolo-[3,4-d]pyridazinones, processes for their preparation, pharmaceutical compositions containing them, a process for preparing the pharmaceutical compositions, and methods of treatment involving their use.

In accordance with the present invention, there is provided a compound of the general formula

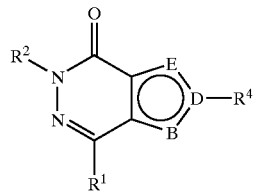

(I)

wherein B represents a group CH or a nitrogen (N), sulfur (S) or oxygen (O) atom; D represents a carbon (C) or nitrogen (N) atom; E represents a group $CR^3$ or a nitrogen (N) atom; when D is a carbon atom, then B is a sulfur or oxygen atom and E is a group $CR^3$, and when D is a nitrogen atom, then either B is a group CH and E is a group $CR^3$ or a nitrogen atom, or B is a nitrogen atom and E is a group $CR^3$; $R^1$ represents a group NR'R" where R' represent a hydrogen atom or a $C_1$–$C_6$ alkyl group, R" represents a $C_1$–$C_6$ alkyl group, or R' and R" together with the nitrogen atom to which they are attached form a 3- to 7-membered saturated heterocyclic ring, or $R^1$ represents a $C_1$–$C_6$ alkyl, $C_1$–$C_6$ alkoxy, $C_1$–$C_3$-alkyloxy$C_1$–$C_3$-alkyl, $C_3$–$C_6$-cycloalkyloxy$C_1$–$C_3$-alkyl, $C_3$–$C_6$ alkenyl, phenyl, $C_3$–$C_7$ cycloalkyl, $C_3$–$C_5$ cycloalkylmethyl or $C_3$–$C_7$ cycloalkenyl group, each of which may be optionally substituted by one or more halogen atoms; $R^2$ represents a methyl group, or a $C_2$–$C_6$ alkyl group optionally substituted by a $C_1$–$C_6$ alkoxy group other than in the 1-position; $R^3$ represents a hydrogen atom or a group X—$R^5$ or X—$Ar^1$; X represents a group —O—, $S(O)_n$, $SO_2N(R^6)$ or $C(=O)N(R^6)$; n is 0, 1 or 2; $R^5$ represents an optionally substituted alkyl or alkenyl group, or, additionally, in the case where X represents $SO_2N(R^6)$ or $C(=O)N(R^6)$, $R^5$ and $R^6$ together with the nitrogen atom to which they are attached may form an optionally substituted 3- to 7-membered heterocyclic ring; $Ar^1$ represents an optionally substituted phenyl or pyridyl group; $R^6$ represents a hydrogen atom, $C_1$–$C_6$ alkyl or is linked to $R^5$ as defined above; $R^4$ represents a group $CHR^7Ar^2$ or $Ar^3$ or, additionally, in the case where D represents a carbon atom, a group $C(O)Ar_2$ or $CR^7(OH)Ar^2$; $Ar^2$ represents an aryl or heteroaryl group which may be optionally substituted; $Ar^3$ represents an acenaphthenyl, indanyl or fluorenyl group, each of which may be optionally substituted; and $R^7$ represents a hydrogen atom or a $C_1$–$C_4$ alkyl group; or a pharmaceutically-acceptable salt or solvate thereof.

In the present specification, unless otherwise indicated, an alkyl or alkenyl substituent or an alkyl moiety in an alkoxy, alkoxycarbonyl, (di)alkylamino, acylamino, alkylsulfonamido, alkylamido or (di)alkylsulfamoyl substituent group may be linear or branched. Furthermore, the alkyl moieties in a dialkylamino or dialkylsulfamoyl substituent group may be the same or different.

$R^1$ represents a group NR'R" where R' represent a hydrogen atom or a $C_1$–$C_6$ alkyl, preferably $C_1$–$C_4$ alkyl, group, R" represents a $C_1$–$C_6$ alkyl, preferably $C_1$–$C_4$ alkyl, group, or R' and R" together with the nitrogen atom to which they are attached form a 3- to 7-membered saturated heterocyclic ring, or $R^1$ represents a $C_1$–$C_6$, preferably $C_3$–$C_5$, alkyl group (e.g. propyl, isopropyl, butyl or isobutyl), a $C_1$–$C_6$ alkoxy group (e.g. methoxy, ethoxy, propoxy, isopropoxy, butoxy, pentoxy or hexoxy), $C_1$–$C_3$-alkyloxy$C_1$–$C_3$-alkyl (e.g. —CH$_2$—O—CH$_3$), $C_3$–$C_6$-cycloalkyloxy$C_1$–$C_3$-alkyl (e.g. —CH$_2$—O-cyclopropyl, —CH$_2$—O-cyclobutyl or —CH$_2$—O-cyclopentyl), a $C_3$–$C_6$ alkenyl group (e.g. propenyl or butenyl), a phenyl group, a $C_3$–$C_7$, preferably $C_3$–$C_5$, cycloalkyl group (e.g. cyclopropyl, cyclobutyl or cyclopentyl), a $C_3$–$C_5$ cycloalkylmethyl group (e.g. cyclopropylmethyl, cyclobutylmethyl or cyclopentylmethyl), or a $C_3$–$C_7$, preferably $C_3$–$C_5$, cycloalkenyl group (e.g. cyclopropenyl, cyclobutenyl or cyclopentenyl, each of which may be optionally substituted by one or more, preferably one to four, e.g. one or two, halogen atoms (e.g. fluorine or chlorine). Where $R^1$ groups contain a double bond the first carbon atom of the $R^1$ group cannot be part of the olefin.

$R^2$ represents a methyl group, or a $C_2$–$C_6$, preferably $C_2$–$C_4$, alkyl group optionally substituted by a $C_1$–$C_6$, preferably $C_1$–$C_4$, alkoxy group (e.g. methoxy, ethoxy, propoxy, isopropoxy, butoxy or isobutoxy) other than in the 1-position. Thus, the alkoxy substituent, if present, is attached to a carbon atom other than the carbon atom which is directly bonded to the ring nitrogen atom.

$R^3$ represents a hydrogen atom or a group X—$R^5$ or X—$Ar^1$.

X represents a group —O—, $S(O)_n$ where n is 0, 1 or 2 or a group $SO_2N(R^6)$ or $C(=O)NR^6$. Preferably X represents a group —O—, $S(O)_n$ where n is 0, 1 or 2, or a group $C(=O)NR^6$.

The group $R^5$ represents an optionally substituted alkyl or alkenyl group, or, additionally, in the case where X represents $SO_2N(R^6)$ or $C(=O)N(R^6)$, $R^5$ and $R^6$ together with the nitrogen atom to which they are attached may form an optionally substituted 3- to 7-membered heterocyclic ring. If $R^5$ represents an optionally substituted alkyl group, the alkyl group will preferably contain from 2 to 10, particularly from 2 to 6, carbon atoms or if $R^5$ represents an optionally substituted alkenyl group, the alkenyl group will preferably contain from 3 to 10, particularly from 3 to 6, carbon atoms. $R^5$ groups cannot form enamines or enol ethers. The alkyl or alkenyl group or heterocyclic ring may be substituted preferably by one or more, e.g. one, two, three or four, substituents independently selected from amido, amino, carboxyl, cyano, hydroxyl, $C_1$–$C_6$ alkoxy (preferably $C_1$–$C_4$ alkoxy), $C_1$–$C_6$ alkylthio (preferably $C_1$–$C_4$ alkylthio), $C_1$–$C_6$ alkylcarbonyl (preferably $C_1$–$C_4$ alkylcarbonyl), $C_1$–$C_6$ alkoxycarbonyl (preferably $C_1$–$C_4$ alkoxycarbonyl), $C_3$–$C_7$ cycloalkyl (preferably $C_5$–$C_6$ cycloalkyl), (di) $C_1$–$C_6$ alkylamino (preferably (di)methylamino or (di)ethylamino), $C_2$–$C_6$ acylamino (preferably $C_2$–$C_4$ acylamino), $C_1$–$C_6$ alkylsulfonamido (preferably $C_1$–$C_4$ alkylsulfonamido), tetrahydrofuranyl, dioxolanyl, imidazolyl, halo$C_1$–$C_6$alkylsulfonamido and tetrazolyl. Especially preferred substituent groups are hydroxyl, carboxyl, methoxy, methylthio, methylcarbonyl, cyclopentyl, —NHC(O)CH$_3$, tetrahydrofuranyl, dioxolanyl and imidazolyl groups.

$Ar^1$ represents an optionally substituted phenyl or pyridyl group. The phenyl or pyridyl group may be substituted preferably by one or more, e.g. one to four, substituents independently selected from carboxyl, hydroxyl, $C_2$–$C_6$, preferably $C_2$–$C_4$, acylamino, $C_1$–$C_6$, preferably $C_1$–$C_4$, alkylamido, $C_1$–$C_6$, preferably $C_1$–$C_4$, alkylsulfonamido and (di)$C_1$–$C_6$, preferably $C_1$–$C_4$, alkylsulfamoyl. The group $Ar^1$ is preferably a pyridyl, particularly 2-pyridyl, group.

$R^4$ represents a group $CHR^7Ar^2$ or $Ar^3$ or, additionally, in the case where D represents a carbon atom, a group $C(O)Ar^2$ or $CR^7(OH)Ar^2$. $R^4$ is preferably a group $CHR^7Ar^2$, $C(O)Ar^2$ or $CR^7(OH)Ar^2$.

$R^7$ represents a $C_1$–$C_4$ alkyl group (e.g. methyl or ethyl) or, most preferably, a hydrogen atom.

$Ar^2$ represents an aryl or heteroaryl group which may be optionally substituted. Examples of suitable aryl and heteroaryl groups include phenyl, naphthyl, pyridyl, quinolinyl, isoquinolinyl, naphthyridinyl, cinnolinyl, phthalazinyl, quinazolinyl, quinoxalinyl, thienyl, benzothienyl, furanyl, benzofuranyl, thiazolyl, benzothiazolyl, indolyl, indolizinyl, pyrazolyl, indazyl, imidazolyl, benzimidazolyl, imidazopyridyl, triazolyl, benzotriazolyl and triazolopyridyl. C The $Ar^2$ group may be optionally substituted by one or more, preferably one to four, especially one to three, substituent groups independently selected from halogen (e.g. fluorine, chlorine, bromine or iodine), trifluoromethyl, trifluoromethoxy, amino, cyano, carboxyl, nitro, $C_1$–$C_6$, preferably $C_1$–$C_4$, alkyl, $C_1$–$C_6$, preferably $C_1$–$C_4$, alkoxy, (di)$C_1$–$C_6$, preferably $C_1$–$C_4$, alkylamino, $C_2$–$C_6$, preferably $C_2$–$C_4$, acylamino, $C_1$–$C_6$, preferably $C_1$–$C_4$, alkylsulfonamido, CONH—($C_1$–$C_6$, preferably $C_1$–$C_4$, alkyl), and $C_1$–$C_6$, preferably $C_1$–$C_4$, alkoxycarbonyl.

$Ar^2$ is preferably a phenyl, naphthyl, pyridyl, quinolinyl or imidazopyridyl group which may be optionally substituted by one to three substituents independently selected from halogen, cyano, trifluoromethyl and $C_1$–$C_6$ alkoxy (especially methoxy).

$Ar^3$ represents an acenaphthenyl, indanyl or fluorenyl group, each of which may be optionally substituted by one or more, e.g. one to four, substituent groups. The optional substituents may be the same as those for $Ar^2$.

Preferred compounds of the invention include:

2,6-Dihydro-2-methyl-4-(2-methylpropyl)-6-(1-naphthalenylmethyl)-1H-pyrrolo[3,4-d]pyridazin-1-one, 2,6-Dihydro-2-(2-methoxyethyl)4-(2-methylpropyl)-6-(1-naphthalenylmethyl)-1H-pyrrolo[3,4-d]pyridazin-1-one, 2,6-Dihydro-7-[(3-hydroxypropyl)thio]-2-methyl-4-(2-methylpropyl)-6-(1-naphthalenylmethyl)-1H-pyrrolo[3,4-d]pyridazin-1-one, 4-{[2,6-Dihydro-2-methyl-4-(2-methylpropyl)-6-(1-naphthalenylmethyl)-1-oxo-1H-pyrrolo[3,4-d]pyridazin-7-yl]thio}butanoic acid, 2,6-Dihydro-7-[(3-hydroxypropyl)sulfinyl]-2-methyl-4-(2-methylpropyl)-6-(1-naphthalenylmethyl)-1H-pyrrolo[3,4-d]pyridazin-1-one, 2,6-Dihydro-7-[(3-hydroxypropyl)sulfonyl]-2-methyl-4-(2-methylpropyl)-6-(1-naphthalenylmethyl)-1H-pyrrolo[3,4-d]pyridazin-1-one, 2-[1-Hydroxy-1-(1-naphthalenyl)methyl]-5-methyl-7-(2-methylpropyl)thieno[2,3-d]pyridazin-4(5H)-one, 5-Methyl-7-(2-methylpropyl)-2-(1-naphthalenylmethyl)thieno[2,3-d]pyridazin-4(5H)-one, 3-[(3-Hydroxypropyl)thio]-5-methyl-7-(2-methylpropyl)-2-(1-naphthalenylmethyl)-thieno[2,3-d]pyridazin-4(5H)-one, 5-Methyl-7-(2-methylpropyl)-2-(1-naphthalenylcarbonyl)thieno[2,3-d]pyridazin-4(5H)-one, 3-[(3-Hydroxypropyl)sulfinyl]-5-methyl-7-(2-methylpropyl)-2-(1-naphthalenyl-methyl)thieno[2,3-d]pyridazin-4(5H)-one, 4{[4,5-Dihydro-5-methyl-7-(2-methylpropyl)-2-(1-naphthalenylmethyl)-4-oxothieno[2,3-d]pyridazin-3-yl]thio}butanoic acid, 5-Methyl-7-(2-methylpropyl)-2-(1-naphthalenylmethyl)-3-(2-pyridinylthio)thieno[2,3-d]pyridazin-4(5H)-one, 3-[(3-Hydroxypropyl)sulfonyl]-5-methyl-7-(2-methylpropyl)-2-(1-naphthalenyl-methyl)thieno[2,3-d]pyridazin-4(5H)-one, 2-[1-Hydroxy-1-phenylmethyl]-5-methyl-7-(2-methylpropyl)thieno[2,3-d]pyridazin-4(5H)-one, 5-Methyl-7-(2-methylpropyl)-2-phenylmethylthieno[2,3-d]pyridazin-4(5H)-one, 3-[(3-Hydroxypropy)thio)]-5-methyl-7-(2-methylpropyl)-2-phenylmethylthieno[2,3-d]pyridazin-4(5H)-one, 3-[(3-Hydroxypropyl)sulfonyl]-5-methyl-7-(2-methylpropyl)-2-phenylmethylthieno-[2,3-d]pyridazin-4(5H)-one, 2,6-Dihydro-2-methyl-4-(2-methylpropyl)-6-phenylmethyl-1H-pyrrolo[3,4-d]pyridazin-1-one, 2,6-Dihydro-2-methyl-4-(2-methylpropyl)-6-phenylmethyl-7-(2-pyridinylthio)-1H-pyrrolo[3,4-d]pyridazin-1-one, 2,6-Dihydro-7-[(3-hydroxypropyl)thio]-2-methyl-4(2-methylpropyl)-6-phenylmethyl-1H-pyrrolo[3,4-d]pyridazin-1-one, 2,6-Dihydro-2-methyl-4-(2-methylpropyl)-6-(3,4,5-trimethoxyphenyl)methyl-1H-pyrrolo[3,4-d]pyridazin-1-one, 2,6-Dihydro-2-methyl-6-(1-naphthalenylmethyl)-4(1-methylethyl)amino-1H-pyrrolo[3,4-d]pyridazin-1-one, 2,6-Dihydro-2-methyl-4-(2-methylpropyl)-6-(4-pyridinyl)methyl-1H-pyrrolo[3,4-d]pyridazin-1-one, 6-(2-Chlorophenyl)methyl-2,6-dihydro-2-methyl-4-(2-methylpropyl)-1H-pyrrolo[3,4-d]pyridazin-1-one, 6-(3,5-Difluorophenyl)methyl-2,6-dihydro-2-methyl-4-(2-methylpropyl)-1H-pyrrolo[3,4-d]pyridazin-1-one, 6-(2-Chloro-6-fluorophenyl)methyl-2,6-dihydro-2-methyl-4-(2-methylpropyl)-1H-pyrrolo[3,4-d]pyridazin-1-one, 6-(3-Chloro-2-fluorophenyl)methyl-2,6-dihydro-2-methyl-4-(2-methylpropyl)-1H-pyrrolo[3,4-d]pyridazin-1-one, 2,6-Dihydro-2-methyl-4-(2-methylpropyl)-6-(2-quinolinylmethyl)-1H-pyrrolo[3,4-d]pyridazin-1-one, 2,6-Dihydro-2-methyl-4-(2-methylpropyl)-6-(2-trifluoromethylphenyl)methyl-1H-pyrrolo[3,4-d]pyridazin-1-one, 2,6-Dihydro-6-(2-imidazo[1,2-a]pyridinyl)methyl-2-methyl-4-(2-methylpropyl)-1H-pyrrolo[3,4-d]pyridazin-1-one, 2,6-Dihydro-N-[3-(1-1H-imidazolyl)propyl]-2-methyl-4-(2-methylpropyl)-1-oxo-6-phenylmethyl-1H-pyrrolo[3,4-d]pyridazin-1-one-5-carboxamide, 2,5-Dihydro-5-methyl-7-(2-methylpropyl)-2-(1-naphthalenylmethyl)-4H-pyrazolo[3,4-d]pyridazin-4-one, 2,6-Dihydro-6-methyl-4-(2-methylpropyl)-2-(1-naphthalenylmethyl)-7H-pyrazolo[3,4-d]pyridazin-7-one, 2,5-Dihydro-3-[(3-hydroxypropyl)thio]-5-methyl-7-(2-methylpropyl)-2-(1-naphthalenylmethyl)-4H-pyrazolo[3,4-d]pyridazin-4-one, 2-[1-Hydroxy-1-(1-naphthalenyl)methyl]-5-methyl-7-(2-methylpropyl)furo[2,3-d]pyridazin-4(5H)one, 5-Methyl-7-(2-methylpropyl)-2-(1-naphthalenylmethyl)furo[2,3-d]pyridazin-4(5H)one, 2-[1-Hydroxy-1-(3-cyanophenyl)methyl]-5-methyl-7-(2-methylpropyl)furo[2,3-d]pyridazin-4(5H)one, 2-(3-Cyanophenyl)methyl-5-methyl-7-(2-methylpropylfuro[2,3-d]pyridazin-4(5H)one, 2-(2-Trifluoromethylphenyl)methyl-5-methyl-7-(2-methylpropy)thieno[2,3-d]pyridazin-4(5H)-one, 2-[(1-Hydroxy-1-pyridin-3-yl)methyl]-5-methyl-7-(2-methylpropyl)thieno[2,3-d]pyridazin-4(5H)-one hydrochloride, 5-Methyl-7-(2-methylpropyl)-2-(3-pyridinylmethyl)thieno[2,3-d]pyridazin-4(5H)-one, 2-(2-Chloro-6-fluorophenyl)methyl-5-methyl-7-(2-methylpropyl)thieno[2,3-d]pyridazin-4(5H)-one, 2-[(1-Hydroxy-1-quinolin-3-yl)methyl]-5-methyl-7-(2-methylpropyl)thieno[2,3-d]pyridazin-4(5H)-one, 5-Methyl-7-(2-methylpropyl)-2-(3-quinolinylmethyl)thieno[2,3-d]pyridazin-4(5H)-one hydrochloride, 2-(3-Chlorophenyl)methyl-3-(2-hydroxyethoxy)-7-(methoxymethyl)-5-methylthieno[2,3-d]pyridazin-4(5H)-one, 2-[(3-Chlorophenyl)methyl]-7-cyclohexyl-3-(2-hydroxyethoxy)-5-methylthieno[2,3-d]pyridazin-4(5H)-one, 2-[(3-Chlorophenyl)methyl]-3-(2-hydroxyethoxy)-5-methyl-7-phenylthieno[2,3-d]pyridazin-4(5H)-one, 2-[(3-Chlorophenyl)methyl]-7-cyclopentyl-3-(2-hydroxyethoxy)-5-methylthieno[2,3-d]pyridazin-4(5H)-one, 7-Cyclopropylmethyl-3-methoxy-5-methyl-2-[(3-trifluoromethylphenyl)methyl]thieno[2,3-d]pyridazin-4(5H)-one, 7-Cyclopropylmethyl-5-methyl-3-[2-(methylthio)ethoxy]-2-[(3-trifluoromethylphenyl)methyl]thieno[2,3-d]pyridazin-4(5H)-one, 7-Cyclopropylmethyl-3-(2-methoxyethoxy)5-methyl-2-[(3-trifuoromethyl-phenyl)methyl]thieno[2,3-d]pyridazin-4(5H)-one, 3-Cyclopentylmethoxy-7cyclopropylmethyl-5-methyl-2-[(3-trifluoromethyl-phenyl)methyl]thieno[2,3-d]pyridazin-4(5H)-one, 7-Cyclopropylmethyl-5-methyl-3-(tetrahydrofuran-2-ylmethoxy)-2-[(3-trifluoromethylphenyl)methyl]thieno[2,3-d]pyridazin-4(5H)-one, 7-Cyclopropylmethyl-3-(3-hydroxy-3methyl-butoxy)-5-methyl-2-[(3-trifluoromethyl-phenyl)methyl]thieno[2,3-d]pyridazin-4(5H)-one, N-{(3-[7-Cyclopropylmethyl-5-methyl-4-oxo-2-[(3-trifluoromethylphenyl)methyl]-4,5-dihydrothieno[2,3-d]pyridazin-3-yl]oxypropyl}acetamide, 7-Cyclopropylmethyl-3-([1,3]dioxolan-4-ylmethoxy)-5-methyl-2-[(3-trifluoromethyl-phenyl)methyl]thieno[2,3-d]pyridazin-4(5H)-one, and 7-Cyclopropylmethyl-5-methyl-3-(4oxopentyl)oxy-2-[(3-trifluoromethyl-phenyl)methyl]thieno[2,3-d]pyridazin-4(5H)-one.

The present invention further provides a process for the preparation of a compound of formula (I) as defined above which comprises:

(a) when X represents $S(O)_n$ and n is 1 or 2, oxidising a compound of general formula

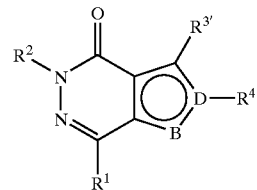

(II)

wherein $R^3$ represents $S-R^5$ or $S-Ar^1$ and B, D, $R^1$, $R^2$, $R^4$, $R^5$ and $Ar^1$ are as hereinbefore defined, in the presence of an appropriate quantity of a suitable oxidising agent (e.g. 3-chloroperoxybenzoic acid or potassium peroxymonosulfate, commercially sold under the trade mark "OXONE") and an appropriate organic solvent (e.g. dichloromethane) under conditions which are well known to those skilled in the art; or (b) when X represents $S(O)_n$ and n is 0, reacting a corresponding compound of formula (I) in which E is $CR^3$ and $R^3$ is a hydrogen atom, with a compound of general formula (III), $R^8-S-S-R^8$, when the groups $R^8$ both represent $R^5$ or $Ar^1$ as previously defined, or with a compound of general formula (IV), $L-S-R^8$, wherein L represents a leaving group such as an arylsulfinate group and $R^8$ is as defined above, in the presence of lithium diisopropylamide (LDA) at a temperature from −78° C. to ambient temperature (20° C.); or (c) when X represents $SO_2N(R^6)$, reacting a compound of general formula

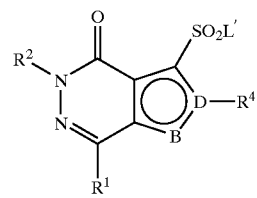

(V)

wherein L' represents a leaving group such as a halogen atom (e.g. chlorine) and B, D, $R^1$, $R^2$ and $R^4$ are as defined above, with a compound of general formula (VI), $HNR^6R^8$, wherein $R^6$ and $R^8$ are as hereinbefore defined, e.g. in an aqueous solution of sodium hydrogen carbonate; or (d) when X represents $C(=O)N(R^6)$, reacting a compound of general formula

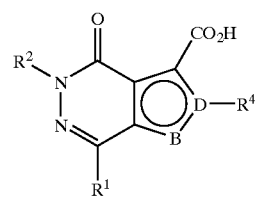

(VII)

wherein B, D, $R^1$, $R^2$ and $R^4$ are as hereinbefore defined with a compound of formula (VI) as defined above, in the presence of 1-(3-dimethylaminopropyl)-3-ethylcarbodiimide and 1-hydroxybenzotriazole hydrate in the presence of a solvent such as dimethylformamide; or (e) when D is a carbon atom, E is $CR^3$, $R^3$ is a hydrogen atom and $R^4$ is $CH(OH)Ar^2$, reacting a compound of general formula

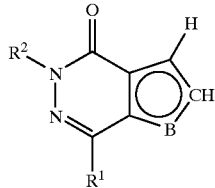
(VIII)

wherein B, $R^1$ and $R^2$ are as hereinbefore defined, with a compound of general formula (IX), $Ar^2CHO$, where $Ar^2$ is as hereinbefore defined, in the presence of lithium diisopropylamide at $-78°$ C. to ambient temperature ($20°$ C.); or (f) when D is a carbon atom, E is $CR^3$, $R^3$ is a hydrogen atom and $R^4$ is $CHR^7Ar^2$, reducing a corresponding compound of formula (I) in which $R^4$ is $CR^7(OH)Ar^2$ (e.g. as prepared in (e) above), in the presence of triethylsilane and trifluoroacetic acid; or (g) when D is a carbon atom, E is $CR^3$, $R^3$ is a hydrogen atom and $R^4$ is $C(O)Ar^2$, oxidising a corresponding compound of formula (I) in which $R^4$ is $CH(OH)Ar^2$ as prepared in (e) above, e.g. in the presence of potassium permanganate; or (h) when D is a carbon atom, E is $CR^3$, $R^3$ is a hydrogen atom, $R^4$ is $CR^7(OH)Ar^2$ and $R^7$ is a $C_1$–$C_4$ alkyl group, reacting a corresponding compound of formula (I) in which $R^4$ is $C(O)Ar^2$ as prepared in (g) above, with a $C_1$–$C_4$ alkylating agent, e.g. a Grignard reagent such as a $C_1$–$C_4$ alkylmagnesium halide, in the presence of a solvent, e.g. tetrahydrofuran; or (i) when D is a carbon atom, E is $CR^3$, $R^3$ is a hydrogen atom and $R^4$ is $Ar^3$, reacting a compound of formula (VIII) as hereinbefore defined, with 1-indanone, 2-indanone, 9-fluorenone or 1-acenaphthenone, in the presence of lithium diisopropylamide and optionally cerium (III) chloride at $-78°$ C. to ambient temperature ($20°$ C.), followed by a reduction reaction, e.g. in the presence of triethysilane and trifluoroacetic acid; or (j) when D is a nitrogen atom, B is CH, E is $CR^3$ and $R^3$ is a hydrogen atom, reacting a compound of general formula

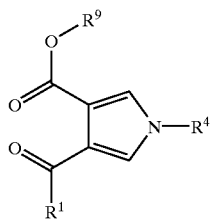
(X)

wherein $R^9$ is an alkyl group (e.g. $C_1$–$C_6$ alkyl such as methyl) and $R^1$ and $R^4$ are as previously defined, with a compound of general formula (XI), $R^2NHNH_2$, wherein $R^2$ is as previously defined, in the presence of a solvent such as ethanol under reflux conditions; or (k) when D is a nitrogen atom, B is CH and E is a nitrogen atom, reacting a compound of general formula

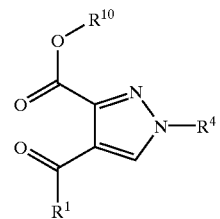
(XII)

wherein $R^{10}$ is an alkyl group (e.g. $C_1$–$C_6$ alkyl such as methyl) and $R^1$ and $R^4$ are as previously defined, with a compound of formula (XI) as previously defined, in the presence of a solvent such as ethanol under reflux conditions;

(l) when D is a nitrogen atom, B is a nitrogen atom, E is $CR^3$ and $R^3$ is a hydrogen atom, reacting a compound of general formula

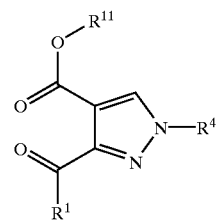
(XIII)

wherein $R^{11}$ is an alkyl group (e.g. $C_1$–$C_6$ alkyl such as methyl) and $R^1$ and $R^4$ are as previously defined, with a compound of formula (XI) as previously defined, in the presence of a solvent such as ethanol under reflux conditions;

(m) when X is —O—, reacting a compound of general formula

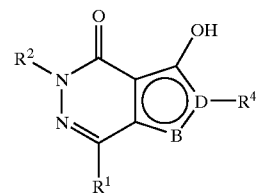
(XIIIA)

wherein B, D, $R^1$, $R^2$ and $R^4$ are as hereinbefore defined, with a compound of general formula (XIIIB), $R^8$-L", wherein L" represents a leaving group such as a halogen atom and $R^8$ is as defined above; or (n) when D is a carbon atom, B is a sulfur or oxygen atom, $R^3$ represents —$OR^5$ and $R^4$ represents $CH_2Ar^2$, reacting a compound of general formula (XIIIC)

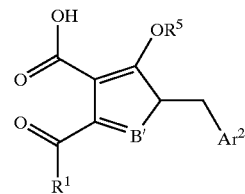
(XIIIC)

wherein B' represents a sulfur or oxygen atom and $R^1$, $R^5$ and $Ar^2$ are as hereinbefore defined, with a compound of formula (XI) as previously defined, in the presence of a solvent such as ethanol under reflux conditions;

and optionally thereafter converting the compound of formula (I) to a further compound of formula (I) and/or forming a pharmaceutically-acceptable salt or solvate of the compound of formula (I).

Compounds of formula (V) may conveniently be prepared by reacting a compound of formula (I) in which E is $CR^3$ and $R^3$ is a hydrogen atom, with sulfur dioxide and lithium diisopropylamide at −78° C., followed by reaction with N-chlorosuccinimide in a solvent (e.g. a two-phase solvent system such as water/hydrochloric acid/dichloromethane).

Compounds of formula (VII) may be readily prepared by reacting a compound of formula (I) in which E is $CR^3$ and $R^3$ is a hydrogen atom, with carbon dioxide in the presence of lithium diisopropylamide.

Compounds of formula (X) may conveniently be prepared by reacting a compound of general formula

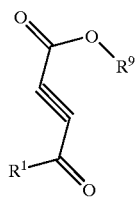

(XIV)

wherein $R^1$ and $R^9$ are as defined above, with a compound of general formula

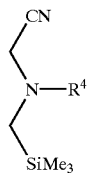

(XV)

wherein $R^4$ is as hereinbefore defined, in the presence of silver fluoride and a suitable solvent such as acetonitrile.

Compounds of formula (X) where $R^4$ is $CH_2Ar^2$ can alternatively be prepared from compounds of general formula

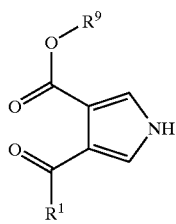

(XVI)

where $R^1$ and $R^9$ are as previously defined, by reacting with a compound of formula (XVII), $Ar^2CH_2L'''$ where $L'''$ is a leaving group such as halogen and $^2Ar$ is as defined above. The reaction can be carried out in the presence of a base in a suitable solvent, for example sodium hydride/dimethylformamide (NaH/DMF), optionally in the presence of potassium iodide (KI).

Compounds of formula (XVI) can be prepared by reacting a compound of general formula

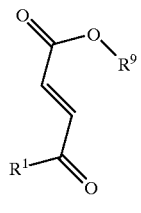

(XVIII)

in which $R^1$ and $R^9$ are as defined above, with tosylmethyl isocyanide. The reaction is suitably carried out in the presence of a base such as sodium hydride in a solvent mixture such as ether/dimethyl sulfoxide.

The preparation of compounds of formulae (XII) and (XIII) is described by the following reaction scheme in which $R \equiv R^{10} \equiv R^{11}$, THF denotes tetrahydrofuran, DMF denotes dimethylformamide, Hal denotes a halogen atom and T denotes an intermediate:

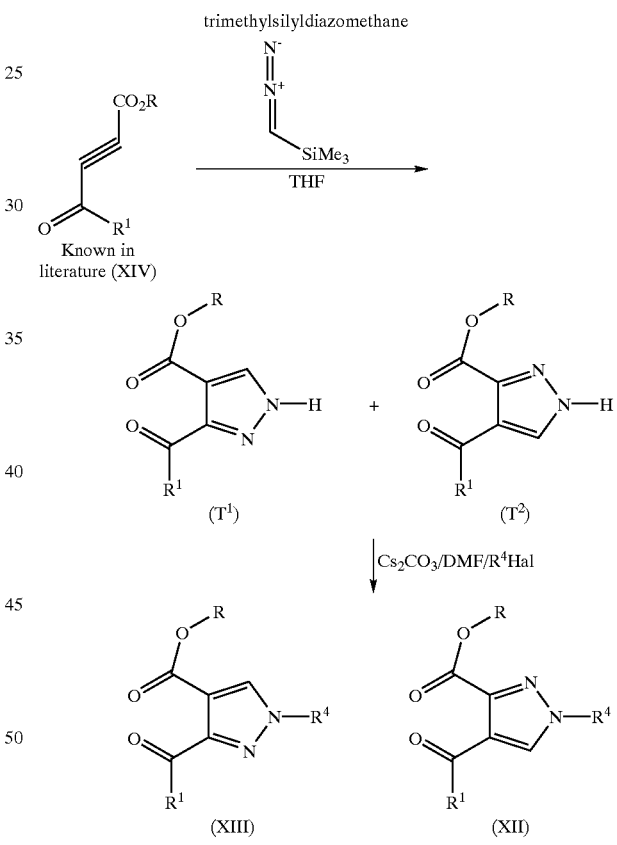

Compounds of formula (XIIIC) can be prepared according to the following reaction scheme:

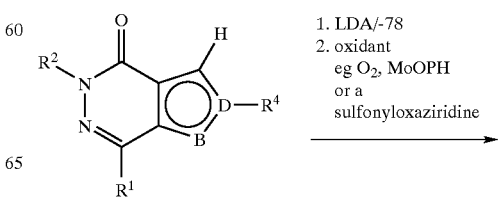

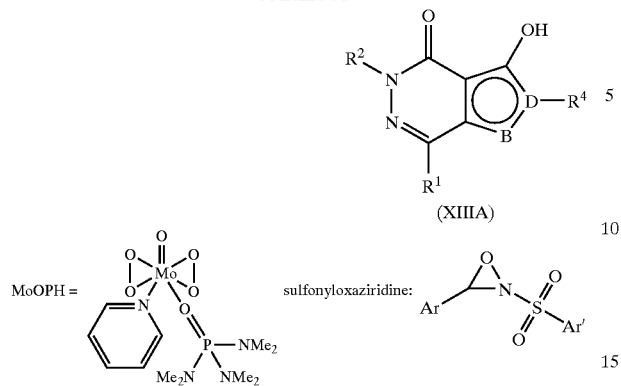

(XIIIA)

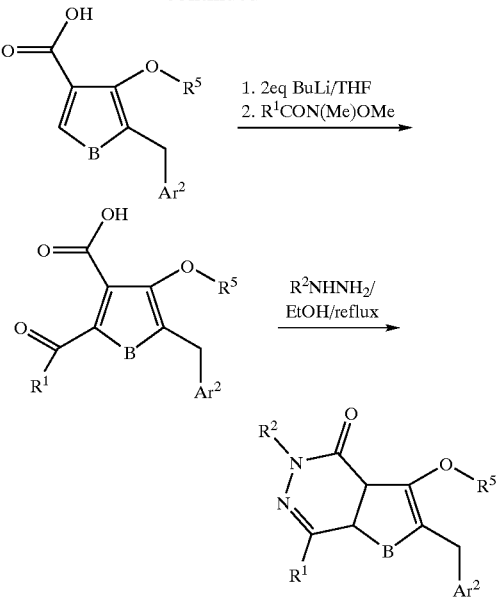

Compounds of formula (XIC) can be prepared according to the following reaction scheme:

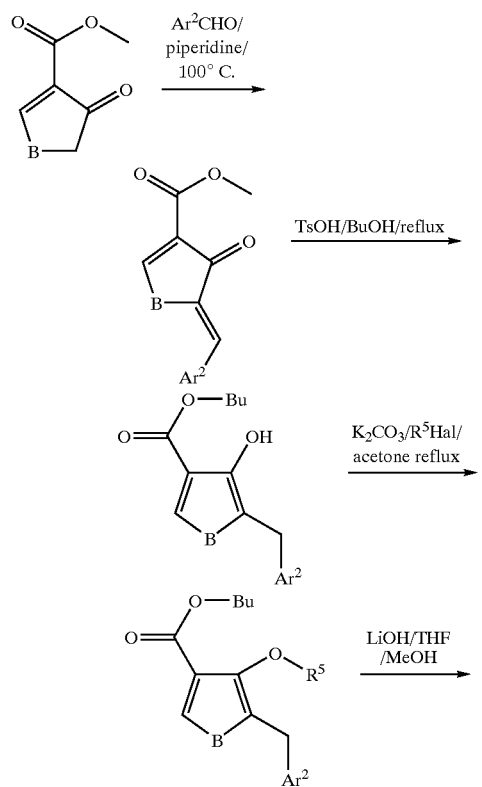

Compounds of formula (III), (IV), (VI), (VIII), (IX), (XI), (XIIIB), (XIV), (XV) and (XVIII) are either commercially available, are well known in the literature or may be prepared easily using known techniques.

Compounds of formula (I) can be converted into further compounds of formula (I) using standard procedures. For example, compounds of formula (I) where $R^5$ represents a hydroxy-substituted alkyl group, e.g. —$(CH_2)_3OH$, can be converted to compounds of formula (I) where $R^5$ represents a cyano-substituted alkyl group, e.g. —$(CH_2)_3CN$, by reaction with methanesulfonyl chloride (MsCl) in the presence of triethylamine and dichloromethane followed by reaction with sodium cyanide in the presence of dimethylformamide. The resulting compounds of formula (I) may in turn be converted into further compounds of formula (I) where $R^5$ represents a tetrazolyl-substituted alkyl group by reaction with trimethyltin azide ($Me_3SnN_3$) in toluene under reflux conditions. These and other conversions are shown by way of illustration in the following reaction scheme in which 'Alk' denotes 'alkyl' and 'Hal' denotes 'halogen':

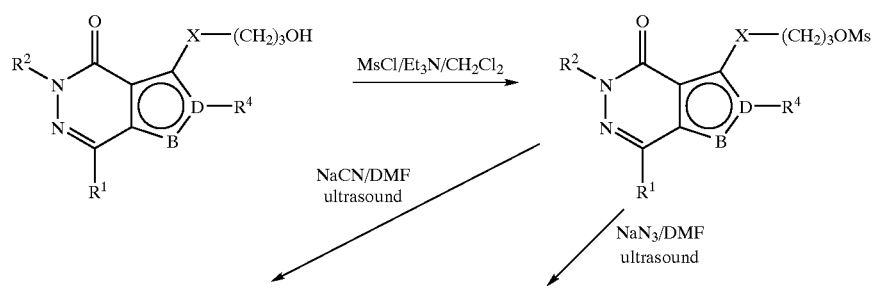

-continued

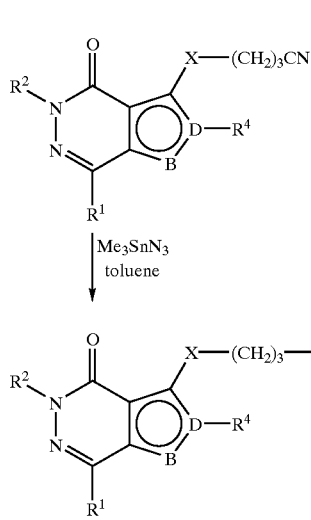
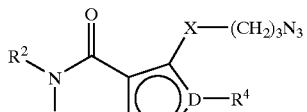
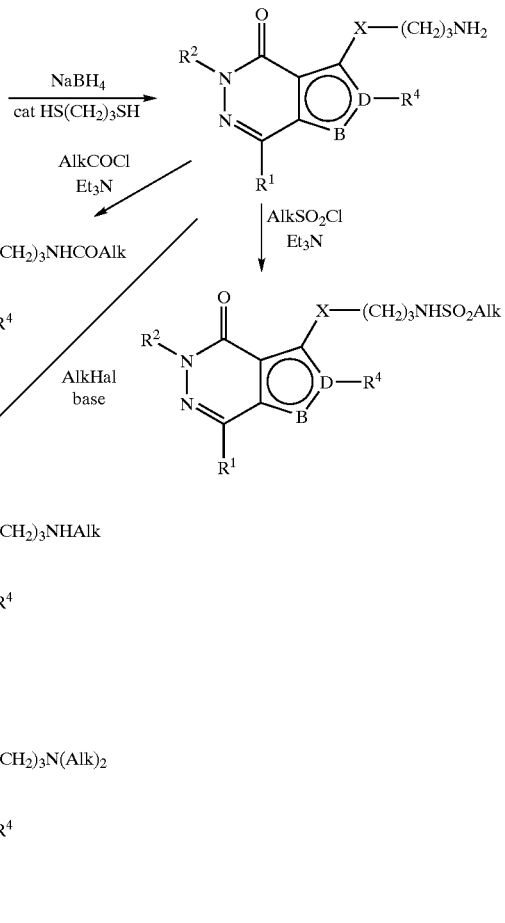

and/or

It will be appreciated by those skilled in the art that in the process of the present invention certain functional groups such as hydroxyl or amino groups in the intermediate compounds may need to be protected by protecting groups. Thus, the final stage in the preparation of the compounds of formula (I) may involve the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically-acceptable salt or solvate thereof, preferably an acid addition salt such as a hydrochloride, hydrobromide, phosphate, acetate, fumarate, maleate, tartrate, citrate, oxalate, methanesulfonate or p-toluenesulfonate, or an alkali metal salt such as a sodium or potassium salt.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compounds of the invention are useful because they possess pharmacological activity in human and non-human animals. They are therefore indicated as pharmaceuticals for use in the (prophylactic) treatment of autoimmune, inflammatory, proliferative and hyperproliferative diseases and immunologically-mediated diseases including rejection of transplanted organs or tissues and Acquired Immunodeficiency Syndrome (AIDS). Examples of these conditions are:

(1) (the respiratory tract) reversible obstructive airways diseases including asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata, allergic conjunctivitis and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease.

The compounds of the invention are also indicated for use as antimicrobial agents, and thus may be used in the treatment of diseases caused by pathogenic micro-organisms.

Accordingly, the present invention provides a compound of formula (I), or a pharmaceutically-acceptable salt or solvate thereof, as hereinbefore defined for use in therapy.

In another aspect, the invention provides the use of a compound of formula (I), or a pharmaceutically-acceptable salt or solvate thereof, as hereinbefore defined in the manufacture of a medicament for use in therapy.

The invention further provides a method of effecting immunosuppression which comprises administering a therapeutically effective amount of a compound of formula (I), or a pharmaceutically-acceptable salt or solvate thereof, as hereinbefore defined to a patient.

The invention still further provides a method of treating, or reducing the risk of, a reversible obstructive airways disease in a patient suffering from, or at risk of, said disease, is which comprises administering to the patient a therapeutically effective amount of a compound of formula (I), or a pharmaceutically-acceptable salt or solvate thereof, as hereinbefore defined.

For the above-mentioned therapeutic uses the dosage administered will, of course, vary with the compound employed, the mode of administration, the treatment desired and the disorder indicated.

The compounds of formula (I) and pharmaceutically-acceptable salts and solvates thereof may be used on their own but will generally be administered in the form of a pharmaceutical composition in which the formula (I) compound/salt/solvate (active ingredient) is in association with a pharmaceutically-acceptable adjuvant, diluent or carrier. Depending on the mode of administration, the pharmaceutical composition will preferably comprise from 0.05 to 99%w (percent by weight), more preferably from 0.10 to 70%w, of active ingredient, and, from 1 to 99.95%w, more preferably from 30 to 99.90%w, of a pharmaceutically-acceptable adjuvant, diluent or carrier, all percentages by weight being based on total composition.

Thus, the present invention also provides a pharmaceutical composition comprising a compound of formula (I), or a pharmaceutically-acceptable salt or solvate thereof, as hereinbefore defined in association with a pharmaceutically-acceptable adjuvant, diluent or carrier.

The invention further provides a process for the preparation of a pharmaceutical composition of the invention which comprises mixing a compound of formula (I), or a pharmaceutically-acceptable salt or solvate thereof, as hereinbefore defined with a pharmaceutically-acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The present invention will be further understood from the following illustrative examples in which, unless otherwise specified, chromatography was carried out over silica and organic solutions were dried over magnesium sulfate. The terms GC, MS, NMR, CDCl$_3$ and DMSO denote respectively gas chromatography, mass spectrometry, nuclear magnetic resonance, chloroform-d and dimethyl sulfoxide.

EXAMPLE 1

2,6-Dihydro-2-methyl-4-(2-methylpropyl)-6-(1-naphthalenylmethyl)-1H-pyrrolo[3,4-d]pyridazin-1-one

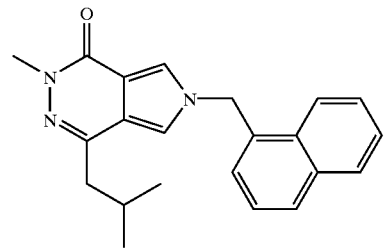

a) (E)-Methyl 6-methyl-4-oxo-2-heptenoate

To 4-methyl-2-pentanone (25 ml) in stirred dry methanol (120 ml) at −2° C. under nitrogen was added bromine (10.0 ml) in one portion. The temperature of the reaction mixture rose to about 5° C. The reaction mixture was stirred at −2° C. for 2 hours until the colour was discharged. Water (100 ml) was added and the mixture was stirred for 16 hours. The reaction mixture was saturated with salt and then extracted with diethyl ether (4 times), which was washed with aqueous sodium hydrogen carbonate solution and then brine. Drying and evaporation gave 1-bromo-4-methyl-2-pentanone as an oil (31 g), contaminated with about 10% of the 3-bromo isomer. GC/MS (EI) 178/180 (M$^+$)

1-Bromo-4methyl-2-pentanone (30 g) in toluene (30 ml) was added over 5 minutes to a stirred suspension of methyl (triphenylphosphoranylidene)acetate (112 g) in dry toluene (300 ml) at 90° C. After 3 hours the thick yellow suspension was cooled and filtered. The filtrate was treated with methyl bromoacetate (16 ml) and the mixture was stirred at 90° C. for 2 hours. On cooling, a precipitate of methoxycarbonylmethyl triphenylphosphonium bromide was filtered off and the filtrate was evaporated to an oil, which was chromatographed with isohexane-dichloromethane (10:1) to afford the sub-title keto ester as an oil (10.2 g).

GC/MS (ET) 170 H$^+$), 113 (BP)

$^1$H NMR (CDCl$_3$): δ0.95 (d, 6H), 2.18 (m, 1H), 2.50 (d, 2H), 3.81 (s, 3H), 6.66 (d, 1H, J=15.9 Hz), 7.06 (d, 1H, J=15.9 Hz)

b) Methyl 4-(3-methyl-1-oxobutyl)-1H-pyrrole-3-carboxylate

A solution of (E)-methyl 6-methyl-4-oxo-2-heptenoate (10 g) prepared as described in a) above and (paratoluenesulfonyl)methyl isocyanide (11.5 g) in a mixture of dry dimethyl sulfoxide (30 ml) and diethyl ether (30 ml) was added over one hour to sodium hydride (2.75 g of a 60% oil dispersion, 0.068 mol) stirred in dry diethyl ether (90 ml) under nitrogen. After a further hour saturated ammonium chloride solution was added and the mixture was extracted with ethyl acetate, which was washed well with water, dried, and evaporated to a gum. The gum was chromatographed with ethyl acetate-isohexane (2:3) to afford a solid (3.3 g) which was crystallised from ethyl acetate-cyclohexane to give the sub-title ester.

Melting point: 136° C.

MS (+ve APCI) (M+H)$^+$210

$^1$H NMR (CDCl$_3$): δ0.96 (d, 6H), 2.22 (m, 1H), 2.78 (d, 2H), 3.83 (s, 3H), 7.26 (t, 1H), 7.37 (t, 1H), 8.8 (br, 1H)

c) Methyl 4-(3-methyl-1-oxobutyl)-1-(1-naphthalenylmethyl)-1H-pyrrole-3-carboxylate To sodium hydride (0.42 g of a 60% oil dispersion, 0.0105 mol), freed from oil, stirred in dry dimethyl formamide (15 ml) under nitrogen was added methyl 4-(3-methyl-1-oxobutyl)-1H-pyrrole-3-carboxylate (2.2 g) prepared as described in b) above in portions over 20 minutes. After 10 minutes, potassium iodide (0.01 g) and (1-naphthalenyl) methyl chloride (1.85 g) in dimethyl formamide (20 ml) were added. The mixture was stirred for 4 hours and then poured into 0.5M hydrochloric acid and extracted with ethyl acetate. The organic layer was washed well with water and then brine, dried and evaporated to a gum, which was chromatographed with ethyl acetate-isohexane (1:3) to give an oil. The oil was crystallised from cyclohexane to yield the subtitle pyrrole (2.6 g).

Melting point: 81–82° C.

MS (APCI) 350 (M+H)$^+$ $^1$H NMR (CDCl$_3$): δ0.94 (d, 6H), 2.2 (m, 1H), 2.76 (d, 2H), 3.79 (s, 3H), 5.50 (s, 2H), 7.17 (d, 1H, J=2.7 Hz), 7.23 (d, 1H, J=2.7 Hz), 7.25 (m, 1H), 7.46 (dd, 1H), 7.55 (m, 2H), 7.80(m, 1H), 7.95 (m, 2H)

d) 2,6-Dihydro-2-methyl-4-(2-methylpropyl)-6-(1-naphthalenylmethyl)-1H-pyrrolo[3,4 d]pyridazin-1-one Methyl 4-(3-methyl-1-oxobutyl)-1-(1-naphthalenyl-methyl)-1H-pyrrole-3-carboxylate (0.35 g) prepared as described in c) above and methylhydrazine (0.10 ml) in ethanol (15 ml) were heated to reflux for 16 hours. The mixture was poured into dilute hydrochloric acid and extracted with ethyl acetate, which was washed with brine, dried, and evaporated to a gum. The gum was chromatographed with ethyl acetate-isohexane (1:1) to afford a solid which was recrystallised from cyclohexane to give 2,6-dihydro-2-methyl-4-(2-methylpropyl)-6-(1-naphthalenylmethyl)-1H-pyrrolo[3,4-d]pyridazin-1-one (0.16 g).

Melting point: 110–112° C.

MS (APCI) 346 (M+H)$^+$ $^1$H NMR (CDCl$_3$): δ0.94 (d, 6H), 2.11 (m, 1H), 2.53 (d, 2H), 3.71 (s, 3H), 5.73 (s, 2H), 7.04 (d, 1H, J=2.1 Hz), 7.22 (d, 1H), 7.52 (d, 1H, J=2.1 Hz), 7.53 (m, 3H), 7.83 (m, 1H), 7.91 (m, 2H)

EXAMPLE 2

2,6-Dihydro-2-(2-methoxyethyl)-4-(2-methylpropyl)-6-(1-naphthalenylmethyl)-1H-pyrrolo[3,4-d]pyridazin-1-one

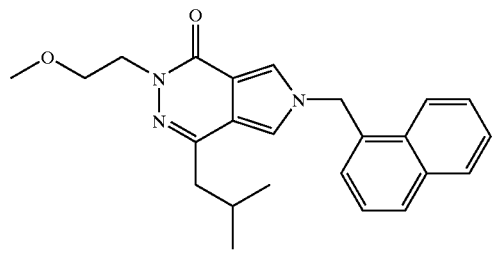

a) 2,6-Dihydro-4-(2-methylpropyl)-6-(1-naphthalenylmethyl)-1H-pyrrolo[3,4-d]pyridazin-1-one Methyl 4-(3-methyl-1-oxobutyl)-1-(1-naphthalenyl-methyl)-1H-pyrrole-3-carboxylate (0.35 g) prepared as described in Example 1c) above and hydrazine hydrate (0.2 ml) were stirred in ethanol (10 ml) for 2 days. The reaction mixture was poured into water to give a solid which was collected and recrystallised from ethyl acetate-cyclohexane to afford the sub-title pyrrole (0.22 g).

Melting point: 183° C.

MS (APCI) 332 (M+H)$^+$ $^1$H NMR (CDCl$_3$): δ0.95 (d, 6H), 2.11 (m, 1H), 2.53 (d, 2H), 5.75 (s, 2H), 7.10 (d, 1H, J=2.1 Hz), 7.26 (m, 1H), 7.52 (d, 1H, J=2.1 Hz), 7.52 (m, 3H), 7.82 (m, 1H), 7.92 (m, 2H), 9.08 (br, 1H)

b) 2,6-Dihydro-2-(2-methoxyethyl)-4-(2-methylpropyl)-6-(1-naphthalenylmethyl)-1H-pyrrolo[3,4-d]pyridazin-1-one 2,6-Dihydro(2-methylpropyl)-6-(1-naphthalenylmethyl)-1H-pyrrolo-[3,4-d]pyridazin-1-one (0.060 g) prepared in a) above was added in portions to sodium hydride (0.020 g of a 60% oil dispersion, 0.5 mmol), freed from oil, and stirred in dry dimethyl formamide under nitrogen. After 0.5 hour, bromoethyl methyl ether (0.04 ml) was added and the reaction mixture was stirred for 16 hours. The mixture was then poured into 0.5M hydrochloric acid and extracted with ethyl acetate, which was washed with brine, dried, and evaporated to an oil. The oil was chromatographed with to ethyl acetate-isohexane (1:1) to give 2,6-dihydro-2-(2-methoxyethyl)-4(2-methylpropyl)-6-(1-naphthalenylmethyl)-1H-pyrrolo[3,4d]pyridazin-1-one (0.027 g).

Melting point: 96–98° C.

MS (APCI) 390 (M+H)$^+$ $^1$H NMR (CDCl$_3$): δ0.94 (d, 6H), 2.11 (m, 1H), 2.53 (d, 2H), 3.35 (s, 3H), 3.75 (t, 2H), 4.32 (t, 2H), 5.72 (s, 2H), 7.02 (d, 1H, J=2.1 Hz), 7.22 (d, 1H), 7.54 (m, 4H), 7.82 (m, 1H), 7.90 (m, 2H)

EXAMPLE 3

2,6-Dihydro-7-[(3-hydroxypropyl)thio]-2-methyl-4 (2-methylpropyl)-6-(1-naphthalenylmethyl)-1H-pyrrolo[3,4-d]pyridazin-1-one

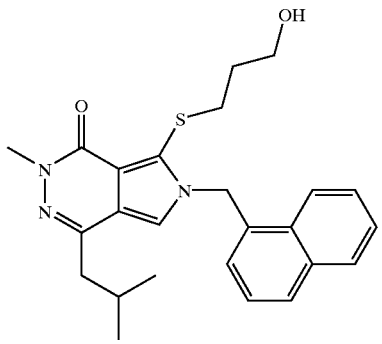

To 2,6-dihydro-2-methyl-4(2-methylpropyl)-6-(1-naphthalenylmethyl)-1H-pyrrolo[3,4-d]pyridazin-1-one (0.345 g) prepared as described in Example 1 above and S-{3-[(1,1-dimethylethyl)dimethylsilyl]oxypropyl} paratoluenethiosulfonate (0.72 g) (J. Med. Chem., 1995, 38, 2557) in dry tetrahydrofuran (10 ml) stirred at −78° C. under nitrogen was added lithium diisopropylamide in tetrahydrofuran (0.39M, 5.1 ml). The reaction mixture was allowed to warm to room temperature overnight and then saturated ammonium chloride solution was added. The mixture was extracted with ethyl acetate, which was then washed with brine, dried, and evaporated to a gum. The gum was chromatographed with ethyl acetate-isohexane (1:1) to give the tertbutyldimethylsilyl ether of the title compound as a solid (0.25 g), MS (APCI) 550 (M+H)$^+$.

To a stirred suspension of this solid (0.25 g) in dry acetonitrile (10 ml) was added 40% hydrofluoric acid (0.07 ml). After 16 hours, aqueous sodium hydrogen carbonate solution was added and the mixture was partially evaporated to leave a residue. The residue was extracted with ethyl acetate, which was washed with brine, dried, and evaporated to a solid. The solid was chromatographed with ethyl acetate-isohexane (3:2) to give, after trituration with diethyl ether-isohexane, 2,6-dihydro-7-[(3-hydroxypropyl)thio]-2-methyl-4-(2-methylpropyl)-6-(1-naphthalenylmethyl)-1H-pyrrolo[3,4-d]pyridazin-1-one (0.17 g).

Melting point: 152° C.

MS (APCI) 436 (M+H)$^+$ $^1$H NMR (CDCl$_3$): δ0.90 (d, 6H), 1.77 (quint, 2H), 1.98–2.12 (m, 1H), 2.48 (d, 2H), 3.12 (t, 2H), 3.75 (s, 3H), 3.87–4.01 (m, 3H), 5.97 (s, 2H), 6.75 (d, 1H), 7.05 (s, 1H), 7.39(dd, 1H), 7.53–7.61 (m, 2H), 7.85 (d, 1H), 7.89–7.95 (m, 2H)

EXAMPLE 4

4-{[2,6-Dihydro-2-methyl-4-(2-methylpropyl)-6-(1-naphthalenylmethyl)-1-oxo-1H-pyrrolo[3,4-d] pyridazin-7-yl]thio}butanoic acid

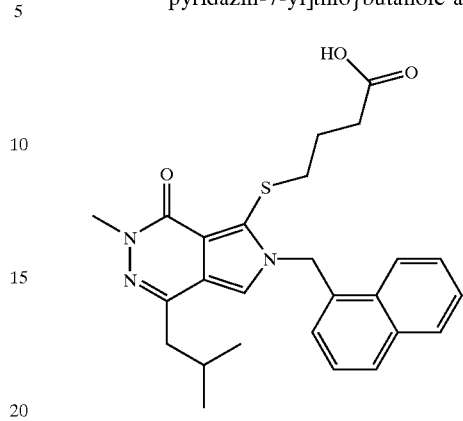

a) S-{3-[4-methyl-2,6,7-trioxabiclclo[2.2.2]octane-1-yl]propyl}paratoluenethiosulfonate To 1-(3-bromopropyl)-4-methyl-2,6,7-trioxabicyclo [2.2.2]octane (Tetrahedron Lett. 1983, 24, 5571) (9.4 g) and triethylamine (5 ml) in dry hexamethylphosphoramide (15 ml) was added potassium paratoluenethiosulfonate (8.5 g) and the mixture was stirred for 3 days. Water was added and the resultant precipitate was filtered off and dissolved in ethyl acetate which was then washed with water, dried over sodium sulfate, and evaporated to a residue. The residue was triturated with diethyl ether to afford the sub-title ester as a solid (8.0 g).

MS (APCI) 359 (M+H)$^+$ $^1$H NMR (DMSO-d$_6$): δ0.73 (s, 3H), 1.59 (m, 4H), 2.47 (s, 3H), 2.99 (t, 2H), 3.77 (s, 6H), 7.48 (d, 2H), 7.79 (d, 2H)

b) Methyl 4-{[2,6-dihydro-2-methyl-4-(2-methylpropyl)-6-(1-naphthalenylmethyl)-1-oxo-1H-pyrrolo[3,4-d]pyridazin-7-yl]thio}butanoate To a stirred solution of 2,6-dihydro-2-methyl-4-(2-methylpropyl)-6-(1-naphthalenylmethyl)-1H-pyrrolo[3,4-d]pyridazin-1-one (0.345 g) prepared as described in Example 1 above and S-{3-[4-methyl-2,6,7-trioxabiclo[2.2.2]octan-1-yl]propyl}paratoluenethiosulfonate (0.70 g) prepared in a) above in dry tetrahydrofuran (8 ml) at −78 C. under nitrogen was added dropwise lithium diisopropylamide in tetrahydrofuran (0.39M, 5.1 ml). After one hour, aqueous sodium hydrogen carbonate solution was added and the mixture was extracted with ethyl acetate, which was then washed with brine, dried over sodium sulfate, and evaporated to a gum. The gum was immediately dissolved in methanolic hydrogen chloride solution and after 16 hours the solution was evaporated to leave a residue. The residue was dissolved in ethyl acetate and washed with brine, dried, and evaporated to a gum. Chromatography with ethyl acetate-isohexane (1:3) gave the sub-title ester as a clear oil (0.24 g).

MS (APCI) 478 (M+H)$^+$ $^1$H NMR (CDCl$_3$), salient peaks: δ3.10 (t, 2H), 3.62 (s, 3H), 3.75 (s, 3H), 5.95 (s, 2H), 7.02 (s, 1H)

c) 4-{[2,6-Dihydro-2-methyl-4-(2-methylpropyl)-6-(1-naphthalenylmethyl)-1-oxo 1H-Pyrrolo[3,4-d]pyridazin-7-yl]thio}butanoic acid Methyl 4-{[2,6-dihydro-2-methyl-4(2-methylpropyl)-6-(1-naphthalenylmethyl)-1-oxo-1H-pyrrolo[3,4-d]pyridazin- 7-yl]thio}butanoate (0.24 g) prepared as described in b) above was stirred with lithium hydroxide hydrate (0.060 g) in tetrahydrofuran-water-methanol (3:1:1) for 3 hours. The solution was evaporated and the resulting residue was partitioned between ethyl acetate and dilute hydrochloric acid. The organic layer was washed with brine, dried, and evaporated to a solid, which was chromatographed with ethyl acetate-isohexane to give, after crystallisation from ethyl acetate-cyclohexane, 4-{[2,6-dihydro-2-methyl-4-(2-methylpropyl)-6-(1-naphthalenylmethyl)-1-oxo-1H-pyrrolo[3,4-d]pyridazin-7-yl]thio}butanoic acid (0.075 g).

Melting point: 167° C.

MS (APCI) 464 (M+H)+

$^1$H NMR (CDCl$_3$): δ0.90 (d, 6H), 1.86 (m, 2H), 2.05 (m, 1H), 2.49 (m, 2H), 2.70 (t, 2H), 2.84 (t, 2H), 3.77 (s, 3H), 6.00 (s, 2H), 6.80 (d, 1H), 7.10 (s, 1H), 7.40 (t, 1H), 7.58 (m, 2H), 7.85–7.94 (m, 3H)

EXAMPLE 5

2,6-Dihydro-7-[(3-hydroxypropyl)sulfinyl]-2-methyl-4-(2-methylpropyl)-6-(1-naphthalenylmethyl)-1H-pyrrolo[3,4-d]pyridazin-1-one (A) and 2.6-Dihydro-7-[(3-hydroxypropyl)sulfonyl]-2-methyl-4-(2-methylpropyl)-6-(1-naphthalenylmethyl)-1H-pyrrolo[3,4-d]pyridazin-1-one (B)

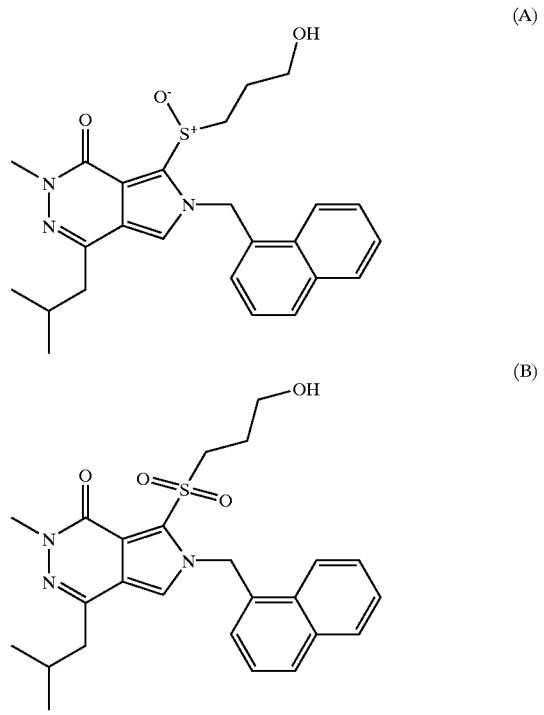

2,6-Dihydro-7-[(3-hydroxypropyl)thio]-2-methyl-4-(2-methylpropyl)-6-(1-naphthalenylmethyl)-1H-pyrrolo[3,4-d]pyridazin-1-one (0.34 g) prepared as described in Example 3 above was dissolved in dichloromethane (7 ml) and 3-chloroperoxybenzoic acid (229 mg) was added. After 4 hours sodium bicarbonate (aqueous) and sodium metabisulfite (aqueous) were added and the mixture was extracted thrice with dichloromethane. The combined organic extracts were washed with brine, dried, filtered and evaporated. The residue was chromatographed eluting with ethyl acetate and then ethyl acetate:ethanol (19:1–9:1) to give 2 products. The more polar product was triturated with ether to give 2,6-Dihydro-7-[(3-hydroxypropyl)sulfinyl]-2-methyl-4-(2-methylpropyl)-6-(1-naphthalenylmethyl)-1H-pyrrolo[3,4-d]pyridazin-1-one (A) (48 mg) whilst the less polar product was recrystallised from isohexane-ethyl acetate to give 2,6-dihydro-7-[(3-hydroxypropyl)sulfonyl]-2-methyl-4-(2-methylpropyl)-6-(1-naphthalenylmethyl)-1H-pyrrolo[3,4-d]pyridazin-1-one (B) (94 mg).

Compound A:

Melting point: 164–166° C. MS (+ve APCI) (M+H)+452

$^1$H NMR (DMSO-d$_6$): δ0.88 (3H, d), 0.89 (3H, d), 1.47–1.65 (2H, m), 1.97–2.10 (1H, m), 2.53 (2H, d), 3.15–3.24 (1H, m), 3.30–3.35 (2H, m), 3.39–3.48 (1H, m), 3.60 (3H, s), 4.56 (1H, t), 6.30 (1H, d), 6.41 (1H, d), 6.73 (1H, d), 7.45 (1H, t), 7.57–7.65 (2H, m), 7.88 (1H, s), 7.91 (1H, d), 7.98–8.02 (1H, m), 8.11–8.14 (1H, m)

Compound B:

Melting point: 150–151° C.

MS (+ve APCI) (M+H)+468

$^1$H NMR (DMSO-d$_6$): δ0.92 (6H, d), 1.57–1.66 (2H, m), 2.10–2.15 (1H, m), 2.60 (2H, d), 3.30–3.36 (2H, m), 3.65 (3H, s), 3.80–3.85 (2H, m), 4.58 (1H, t), 6.35 (1H, d), 6.36 (2H, s), 7.38 (1H, t), 7.58–7.68 (2H, m), 7.86 (1H, d), 8.00 (1H, dd), 8.12 (1H, d), 8.18 (1H, s)

EXAMPLE 6

2-[1-Hydroxy-1-(1-naphthalenyl)methyl]-5-methyl-7-(2-methylpropyl)thieno [2,3-d]pyridazin-4(5H)-one

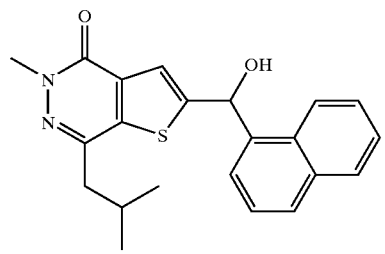

a) 2-(3-Methyl-1-oxobutyl)thiophene-3-carboxylic acid

Lithium diisopropylamide (86 mmol) in tetrahydrofuran (30 ml) was added at 0° C. to a solution of thiophene-3-carboxylic acid (5 g) in tetrahydrofuran (50 ml). Isovaleraldehyde (4.6 ml) was added as a solution in tetrahydrofuran (30 ml) at 0° C. The reaction mixture was stirred at 25° C. for 3 hours and then water (100 ml) was added and the tetrahydrofuran was removed in vacuo. The aqueous residue obtained was extracted with ethyl acetate and the aqueous phase added to potassium permanganate (12.3 g) and warmed to 60° C. for 1.5 hours. The mixture was filtered, allowed to cool to ambient temperature, and then acidified with dilute hydrochloric acid. The acidic aqueous mixture was extracted with ethyl acetate and the organic extract dried and evaporated to give the sub-title compound as an oil (5.3 g).

MS (APCI) ((M−H−)−) 211

$^1$H NMR (CDCl$_3$): δ1.03 (6H, d), 2.37 (1H, m), 2.95 (2H, d), 7.70 (1H, d), 7.97 (1H, d)

b) 5-Methyl-7-(2-methylpropyl)thieno[2,3-d]pyridazin-4(5H)-one 2-(3-Methyl-1-oxobutyl)thiophene-3-carboxylic acid (5.3 g) prepared in a) above was dissolved in ethanol (30 ml) and methylhydrazine (1.5 ml) added. The resultant mixture was heated to reflux for 10 hours. The reaction mixture was evaporated and the residue obtained was dissolved in ethyl acetate. The organic phase was washed twice with dilute hydrochloric acid, twice with saturated sodium hydrogen carbonate solution and once with brine, then dried and evaporated. Purification by chromatography eluting with iso-hexane/ethyl acetate (2:1 to 1:1) gave the sub-title compound as an oil (3.05 g).

MS (APCI) ((M+H)$^+$) 223

$^1$H NMR (CDCl$_3$): δ1.00 (6H, d), 2.05 (1H, m), 2.75 (2H, d), 3.85 (3H, s), 7.60 (1H, d), 7.80 (1H, d)

c) 2-[-Hydroxy-1-(1-naphthalenyl)methyl]-5-methyl-7-(2-methylpropyl)thieno-[2,3-d]pyridazin-4(5H)-one Lithium diisopropylamide (6.75 mmol) in tetrahydrofuran (8 ml) and 1-naphthaldehyde (0.7 ml) in tetrahydrofuran (5 ml) were added alternately to a solution of 5-methyl-7-(2-methylpropyl)thieno[2,3-d]pyridazin-4(5H)-one (1 g) prepared in b) above in tetrahydrofuran (20 ml) at 0° C. After 2 hours, water (10 ml) was added, the reaction mixture was acidified with dilute hydrochloric acid and then extracted with ethyl acetate. The organic phase was washed once with dilute hydrochloric acid, twice with saturated sodium hydrogen carbonate solution and once with brine, before being dried and evaporated. Purification by chromatography eluting with isohexane/ethyl acetate (1:1), and subsequent HPLC eluting with the same gave the title compound (0.4 g).

Melting point: 165–7° C.

MS (APCI) ((M+H)$^+$) 379

$^1$H NMR (DMSO-d$_6$): δ0.91 (6H, d), 2.12 (1, m), 2.57 (2H, d), 3.64 (3H, s), 6.77 (1H, d), 6.84 (1H, d), 7.28 (1H, s), 7.48–53 (2H, m), 7.57 (1H, t), 7.79 (1H, d), 7.92 (1H, d), 7.96 (1H, dd), 8.26 (1H, dd)

EXAMPLE 7

5-Methyl-7-(2-methylpropyl)-2-(1-naphthalenylmethyl)thieno[2,3-d]pyridazin-4(5H)-one

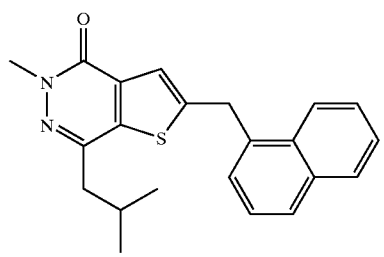

Triethylsilane (0.3 ml) was added to a solution of 2-[1-hydroxy-1-(1-naphthalenyl)methyl]-5-methyl-7-(2-methylpropyl)thieno[2,3-d]pyridazin-4(5H)-one (0.3 g) prepared as described in Example 6 above and trifluoroacetic acid (2 ml) in dichloromethane (10 ml). After 30 minutes, the reaction mixture was evaporated and the residue remaining was dissolved in ethyl acetate. The ethyl acetate solution was washed twice with saturated sodium hydrogen carbonate solution and once with brine, and then dried and evaporated. Purification by chromatography eluting with iso-hexane/ethyl acetate (4:1 to 2:1), and subsequent HPLC eluting with isohexane:ethyl acetate (2:1) gave the title compound (0.25 g).

Melting point: 103° C.

MS (APCI) ((M+H)$^+$) 363

$^1$H NMR (DMSO-d$_6$): δ0.86 (6H, d), 2.04 (1, m), 2.51 (2H, d), 3.65 (3H, s), 4.81 (2H, s), 7.47 (1H, s), 7.48–7.53 (3H, m), 7.60 (1H, d), 7.89 (1H, d), 7.96 (1H, dd), 8.15 (1H, dd)

EXAMPLE 8

3-[(3-Hydroxypropyl)thio]-5-methyl-7-(2-methylpropyl)2-(1-naphthalenylmethyl)-thieno[2,3-d]pyridazin-4(5H)-one

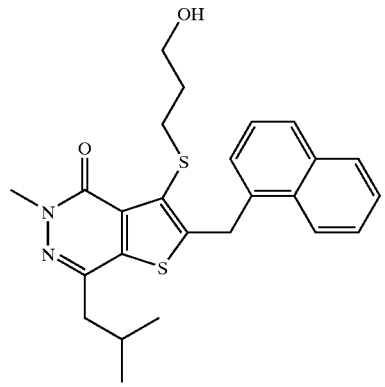

Prepared from 5-methyl-7-(2-methylpropyl)-2-(1-naphthalenylmethyl)thieno[2,3-d]-pyridazin-4(5H)-one (385 mg) prepared as described in Example 7 above and S-{3-[(1,1-dimethylethyl)dimethylsilyl]oxypropyl} para-toluenethiosulfonate (600 mg) (J. Med. Chem., 1995, 38, 2557) following the method of Example 3. Yield 370 mg.

Melting point: 128–130° C.

MS (+ve APCI) (M+H)$^{30}$ 453

$^1$H NMR (DMSO-d$_6$): δ0.83 (6H, d), 1.67 (2H, quin), 1.93–2.06 (1H, m), 2.46 (2H, d), 3.13 (2H, t), 3.50 (2H, q), 3.70 (3H, s), 4.53 (1H, t), 4.88 (2H, s), 7.45–7.58 (4H, m), 7.90 (1H, d), 7.95–8.04 (2H, m)

EXAMPLE 9

5-Methyl-7-(2-methylpropyl)-2-(1-naphthalenylcarbonyl)thieno[2,3-d]pyridazin-4(5H)-one

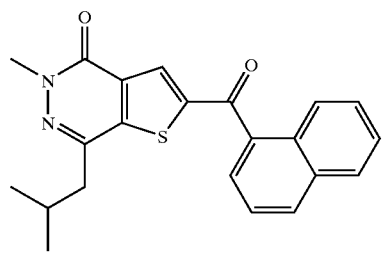

Potassium permanganate (0.335 g) and 18 crown-6 (10 mg) were added to a solution of 2-[1-hydroxy-1-(1-naphthalenyl)methyl]-5-methyl-7-(2methylpropyl)thieno[2,3-d]pyridazin-4(5H)-one (example 7, 0.40 g) in dichloromethane (30 ml) at room temperature. After 1 hour, further potassium permanganate (0.30 g) was added and stirring was continued for a further hour. The mixture was filtered, diluted with dichloromethane (70 ml), washed twice with water then with brine, then dried, filtered and evaporated. The residue was purified by column chromatography, eluting with ethyl acetate:isohexane (1:2), to give the title compound (0.14 g). This was purified further by preparative normal-phase HPLC with gradient ethyl acetate/isohexane elution.

Melting point: 121° C.

MS (+ve APCI) 377 ((M+H)$^+$)

$^1$H NMR (DMSO d6) δ0.98 (6H, d), 2.14–2.26 (1H, m), 2.74 (2H, d), 3.70 (3H, s), 7.60–7.65 (2H, m), 7.70 (1H, dd), 7.79 (1H, s), 7.98 (1H, dd), 8.07–8.11 (2H, m), 8.26 (1H, d).

EXAMPLE 10

3-[(3-Hydroxyprpyl)sulfinyl]-5-methyl-7-(2-methylpropyl)-2-(1-naphthalenyl-methyl)thieno[2,3-d]pyridazin-4(5H)-one

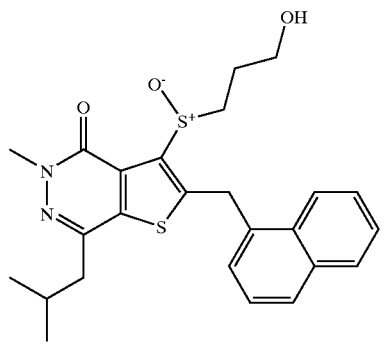

3-Chloroperoxybenzoic acid (80%, 0.055 g) was added to a stirred solution of 3-{[3-hydroxypropyl]thio}5-methyl-7-(2-methylpropyl)-2-(1-naphthalenylmethyl)thieno[2,3-d]pyridazin-4(5H)-one (example 8, 0.14 g) in dichloromethane (20 ml) at room temperature. After 20 hours, the mixture was diluted with dichloromethane (30 ml), washed with saturated sodium hydrogen carbonate solution, dried, filtered and evaporated. The residue was purified by column chromatography, eluting with ethyl acetate:isohexane (1:1 then 2:1), followed by preparative normal-phase BPLC with gradient ethyl acetate/isohexane elution to give the title compound (0.05 g) as a foam.

Melting point: 60–65° C.

MS (+ve APCI) 469 ((M+H)$^+$)

$^1$H NMR (DMSO d6) δ0.80 (3H, d), 0.82 (3H, d), 1.81–1.99 (2H, m), 2.03–2.15 (1H, m), 2.44 (2H, d), 3.28–3.39 (2H, m), 3.58 (2H, q), 3.67 (3H, t), 4.65 (1H, t), 4.84 (1H, d), 5.80 (1H, d), 7.51–7.56 (3H, m), 7.61 (1H, d), 7.92 (1H, d), 7.95–7.99 (1H, m), 8.14–8.17 (1H, m).

EXAMPLE 11

4-{[4,5-Dihydro-5-methyl-7-(2-methylpropyl)-2-(1-naphthalenylmethyl)-4-oxothieno[2,3-d]pyridazin-3-yl]thio}butanoic acid

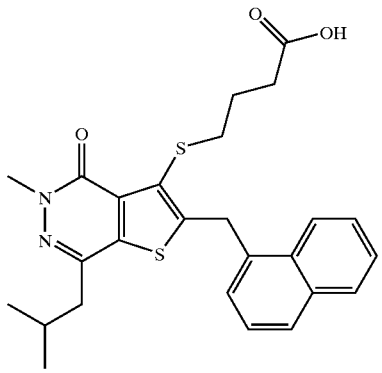

a) 4,4,4-Trimethoxybutyl 4-methylbenzenesulfonothioate

A mixture of para-toluenethiosulfonic acid potassium salt (24 mmol), trimethyl 4-bromoorthobutyrate (22 mmol) and hexamethylphosphoramide (30 ml) was stirred at room temperature for 48 h and was then poured into 10:1 hexane/diethyl ether (500 ml) and shaken vigorously. The mixture was washed with water (2×200 ml) and then brine. The organic phase was collected and dried over MgSO$_4$ and evaporated to yield the sub-title ester as an oil (5.3 g) containing ca 7% 4,4,4-Trimethoxybutyl 4-methylbenzenesulfonodithioate.

$^1$H NMR (CDCl$_3$) δ1.95(2H, m), 2.37(2H, t), 2.44(3H, s), 3.02(2H, t), 3.16(9H, s), 7.33(2H, d), 7.80(2H, d).

b) Methyl 4-{[4,5-dihydro-5-methyl-7-(2-methylpropyl)-2-(1-naphthalenylmethyl)-4-oxothieno[2,3-d]pyridazin-3-yl]thio}butanoate A solution of lithium diisopropylamide (1.8 mmol) in tetrahydrofuran (5 ml) was added dropwise to a solution of 5-methyl-7-(2-methylpropyl)-2-(1-naphthalenyl)methyl)-thieno[2,3-d]pyridazin-4(5H)-one (example 7, 0.30 g) and 4,4,4-trimethoxybutyl 4-methylbenzenesulfonothioate (0.42 g) in tetrahydrofuran (15 ml) at −78° C. under nitrogen. After 2 hours, the mixture was warmed to room temperature, quenched with 1M hydrochloric acid (25 ml) and extracted with ethyl acetate (25 ml). The organic extracts were washed with 1M hydrochloric acid, then with sodium hydrogen carbonate solution, then with brine, dried, filtered and evaporated. The residue was purified by column chromatography, eluting with ethyl acetate:isohexane (1:4, 1:2, 1:1 then 1:0), to give the sub-title compound (0.25 g) as an oil.

MS (+ve APCI) 495 ((M+H)$^+$)

$^1$H NMR (CDCl$_3$) δ0.88 (6H, d), 2.00 (2H, quin), 1.99–2.11 (1H, m), 2.44 (2H, d), 2.55 (2H, t), 3.20 (2H, t), 3.65 (3H, s), 3.82 (3H, s), 4.87 (2H, s), 7.40–7.50 (4H, m), 7.84 (1H, d), 7.90 (1H, dd), 7.98 (1H, dd).

c) 4-{[4,5-Dihydro-5-methyl-7-(2-methylpropyl)-2-(1-naphthalenylmethyl)-4-oxothieno[2,3-d]pyridazin-3-yl]thio}butanoic acid A solution of lithium hydroxide hydrate (0.035 g) in water (1 ml) was added to a solution of methyl 4-{[4,5-dihydro- 5-methyl-7-(2-methylpropyl)-2-(1-naphthalenylmethyl)-4-oxothieno[2,3-d]pyridazin-3-yl]thio}butanoate (0.20 g) in tetrahydrofuran (6 ml) at room temperature. After 2 days, 1M hydrochloric acid (20 ml) was added and the mixture was extracted with ethyl acetate (20 ml). The organic extracts were washed with brine, dried, filtered and evaporated. The residue was dissolved in ethyl acetate:isohexane (1:2) and the precipitated solid was collected. The solid was suspended in boiling ethyl acetate (20 ml), cooled and collected to give the title compound (0.05 g).

Melting point 154–156° C.

MS (+ve APCI) 481 ((M+H)$^+$)

$^1$H NMR (DMSO d6) δ0.85 (6H, d), 1.76 (2H, quin), 1.94–2.06 (1H, m), 2.38 (2H, t), 2.45 (2H, d), 3.11 (2H, t), 3.69 (3H, s), 4.88 (2H, s), 7.45–7.58 (4H, m), 7.90 (1H, d), 7.97–8.01 (2H, m) 12.09 (1H, brs).

EXAMPLE 12

5-Methyl-7-(2-methylpropyl)-2-(1naphthalenylmethyl)-3-(2-pyridinylthio)thieno[2,3-d]pyridazin-4(5H)-one

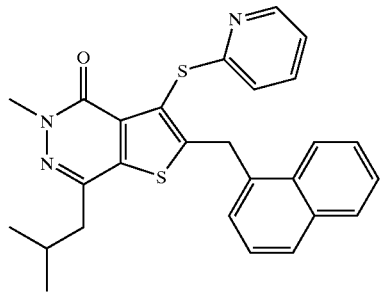

A solution of butyl lithium in hexanes (2.5M, 0.60 ml) was added to a solution of diisopropylamine (0.16 ml) in tetrahydrofuran (5 ml) at 0° C. under nitrogen. After 30 minutes, 4 ml of the resulting solution was added to a solution of 5-methyl-7-(2-methylpropyl)-2-(1-naphthalenylmethyl)thieno[2,3-d]pyridazin-4(5H)-one (example 7, 0.207 g) and 2,2'-dipyridyl disulfide (0.19 g) in tetrahydrofuran (15 ml) at −78° C. The mixture was warmed to room temperature, quenched with saturated aqueous ammonium chloride solution (25 ml) and extracted with ethyl acetate (50 ml). The organic extracts were washed twice with saturated aqueous ammonium chloride solution, twice with saturated sodium hydrogen carbonate solution, then with brine (25 ml), dried, filtered and evaporated. The residue was purified by column chromatography, eluting with ethyl acetate:isohexane (1:2 then 1:1), followed by recrystallisation from ethyl acetate/isohexane and then preparative normal-phase HPLC with gradient ethyl acetate/isohexane elution to give the title compound (0.077 g) as a foam.

MS (+ve APCI) 472 ((M+H)$^+$)

$^1$H NMR (DMSO d6) δ0.85 (6H, d), 1.97–2.08 (1H, m), 2.50 (2H, d), 3.59 (3H, s), 4.83 (2H, s), 7.09 (1H, d), 7.14 (1H, dd), 7.35 (1H, td), 7.48–7.52 (3H, m), 7.66 (1H, td), 7.87–7.96 (3H, m), 8.38–8.40 (1H, m).

EXAMPLE 13

3-[(3-Hydroxypropyl)sulfonyl]-5-methyl-7-(2-methylpropyl)-2-(1-naphthalenyl-methyl)thieno[2,3-d]pyridazin-4(5H)-one

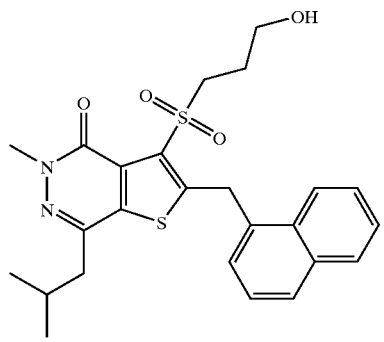

3-Chloroperoxybenzoic acid (80%, 0.27 g) was added to a stirred solution of 3-{[3-hydroxypropyl]thio}5-methyl-7-(2-methylpropyl)-2-(1-naphthalenylmethyl)thieno[2,3-d]pyridazin-4(5H)-one (example 7, 0.28 g) in dichloromethane (10 ml). After 24 hours, the mixture was diluted with dichloromethane (40 ml), washed with saturated sodium hydrogen carbonate solution, dried, filtered and evaporated. The residue was purified by column chromatography, eluting with ethyl acetate:isohexane (1:1 then 2:1 then 1:0), followed by recrystallisation from ethyl acetate/isohexane to give the title compound (0.209 g).

Melting point 160–163° C.

MS (+ve APCI) 485 ((M+H)$^+$)

$^1$H NMR (DMSO d6) δ0.81 (6H, d), 1.87–1.99 (3H, m), 2.45 (2H, d), 3.50 (2H, q), 3.71 (3H, s), 3.96–4.05 (2H, m), 4.70 (1H, t), 5.23 (2H, s), 7.51–7.58 (4H, m), 7.94–8.02 (3H, m).

EXAMPLE 14

2-[-Hydroxy-1-phenylmethyl]-5-methyl-7-(2-methylpropyl)thieno[2,3-d]pyridazin-4(5H)-one

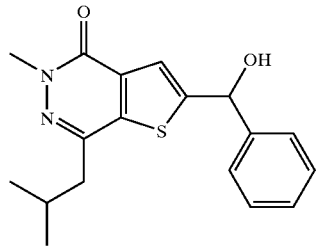

A solution of lithium diisopropylamide (13.6 mmol) in tetrahydrofuran/hexane (2:1, 22 ml) was added dropwise to a solution of 5-methyl-7-(2-methylpropyl)thieno[2,3-d]pyridazin-4(5H)-one (example 6 step b, 2.00 g) in tetrahydrofuran (24 ml) at −70° C. under nitrogen. Benzaldehyde (2.00 ml) was added and after 15 minutes, the mixture was warmed to room temperature. 1M Hydrochloric acid (50 ml) was added and the mixture was extracted with ethyl acetate (100 ml). The organic extracts were washed twice with 1M hydrochloric acid, twice with saturated sodium hydrogen carbonate solution, then with brine, dried, filtered and evaporated. The residue was purified by column chromatography, eluting with ethyl acetate:isohexane (1:3 then 1:2 then 1:1), to give the title compound (2.48 g) of which 0.5 g was purified by preparative normal-phase HPLC with gradient ethanol/dichloromethane elution to gave the title compound (0.38 g) as an oil.

MS (+ve APCI) 329 ((M+H)$^+$)

$^1$H NMR (DMSO d6) δδ0.92 (6H, d), 2.06–2.18 (1H, m), 2.60 (2H, d), 3.67 (3H, s), 6.11 (1H, d), 6.71 (1H, d), 7.28 (1H, t), 7.36 (1H, s), 7.39 (2H, t), 7.49 (2H, d).

EXAMPLE 15

5-Methyl-7-(2-methylpropyl)-2-phenylmethylthieno [2,3-d]pyridazin-4(5H)-one

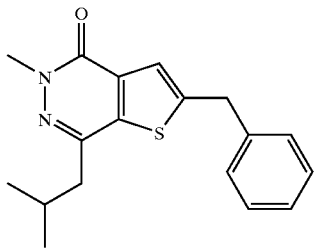

Triethylsilane (1.0 ml) was added to a stirred solution of 2-[1-hydroxy-1-phenylmethyl]-5-methyl-7-(2-methylpropyl)thieno[2,3-d]pyridazin-4(5H)-one (example 14, 1.44 g) in trifluoroacetic acid (2 ml) and dichloromethane (10 ml) at room temperature. After 24 hours, saturated sodium hydrogen carbonate solution (100 ml) was added and the mixture was extracted with ethyl acetate (100 ml). The organic extracts were washed twice with saturated sodium hydrogen carbonate solution, then with brine, and then dried, filtered and evaporated. The residue was purified by column chromatography, eluting with ethyl acetate:isohexane (1:4 then 1:3), to give the title compound (1.11 g) as a solid.

Melting point: 97–98° C.

MS (+ve APCI) 313 ((M+H)$^+$)

$^1$H NMR (DMSO d6) δ0.90 (6H, d), 2.04–2.16 (1H, m), 2.57 (2H, d), 3.67 (3H, s), 4.32 (2H, s), 7.25 (1H, m), 7.30–7.40 (4H, m), 7.44 (1H, s).

EXAMPLE 16

3-[(3-Hydroxypropy)thio]-5-methyl-7-(2methylpropyl)-2phenylmethylthieno[2,3-d] pyridazin-4(5H)-one

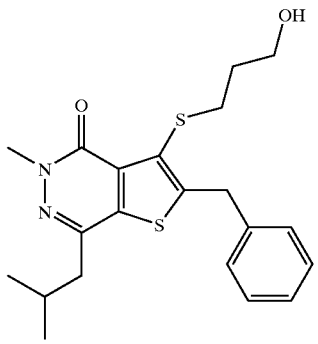

A solution of butyl lithium in hexanes (2.5M, 1.3 ml) was added to a solution of diisopropylamine (0.45 ml) in tetrahydrofuran (6 ml) at 0° C. under nitrogen. After 30 minutes, 5 ml of the resulting solution was added to a solution of 5-methyl-7-(2-methylpropyl)-2-phenylmethylthieno[2,3-d]pyridazin-4(5H)-one (example 15, 0.50 g) and S-[3-{[(1,1-dimethylethyl)dimethylsilyl] oxy}propyl] 4methylbenzenesulfonothioate, (J. Med. Chem. 1995, 38, 2557., 0.85 g) in tetrahydrofuran (10 ml) at −78° C. under nitrogen. The reaction mixture was warmed to room temperature, quenched with saturated aqueous ammonium chloride solution (25 ml) and extracted with ethyl acetate (50 ml). The organic extracts were washed twice with saturated aqueous ammonium chloride solution, twice with saturated sodium hydrogen carbonate solution, then with brine, dried, filtered and evaporated. The residue was dissolved in acetonitrile (20 ml) and treated with 40% hydrofluoric acid (1 ml). After 16 hours, saturated sodium hydrogen carbonate solution (50 ml) was added and the mixture was extracted with ethyl acetate (50 ml). The organic extracts were washed with brine, dried, filtered and evaporated. The residue was purified by column chromatography, eluting with ethyl acetate:isohexane (1:2 then 1:1) to give the title compound (0.51 g) as a solid.

Melting point: 60–65° C.

MS (+ve APCI) 403 ((M+H)$^+$)

$^1$H NMR (DMSO d6) δ0.88 (6H, d), 1.57 (2H, quin), 2.08 (1H, m), 2.53 (2H, d), 3.00 (2H, t), 3.43 (2H, q), 3.70 (3H, s), 4.44 (2H, s), 4.48 (1H, t), 7.22–7.34 (5H, m).

EXAMPLE 17

3-[(3-Hydroxypropyl)sulfonyl]-5-methyl-7-(2-methylpropyl)-2-phenylmethylthieno-[2,3-d] pyridazin-4(5H)-one

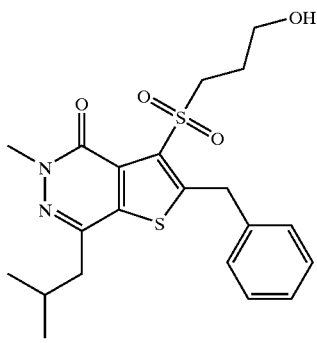

Prepared from 3-{[3-hydroxypropyl)]thio}-5-methyl-7-(2-methylpropyl)-2-phenylmethylthieno[2,3-d]pyridazin-4 (5H)-one (Example 16, 0.32 g) and 3-chloroperoxybenzoic acid (86%, 0.32 g) in dichloromethane (20 ml) according to the procedure of example 13 to give the title compound (0.18 g) as a foam.

Melting point: 105–107° C.

MS (+ve APCI) 435 ((M+H)$^+$)

$^1$H NMR (DMSO d6) δ0.89 (6H, d), 1.74–1.83 (2H, m), 1.99–2.10 (1H, m), 2.57 (2H, d), 3.44 (2H, q), 3.71 (3H, s), 3.86–3,92 (2H, m), 4.63 (1H, t), 4.75 (2H, s), 7.28–7.38 (5H, m).

EXAMPLE 18

2,6-Dihydro-2-methyl-4-(2-methylpropyl)-6-phenylmethyl-1H-pyrrolo[3,4-d]pyridazin-1-one

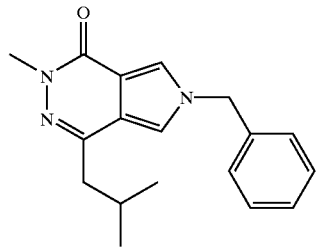

a) 2,6-Dihydro-2-methyl-4-(2-methylpropyl)-1H-pyrrolo[3,4-d]pyridazin-1-one

Methyl 4-(3-methyl-1-oxobutyl)-1H-pyrrole-3-carboxylate (Example 1 step b, 0.7 g) and methylhydrazine (0.6 ml) in ethanol (20 ml) were heated under reflux for 16 hours.

The solution was evaporated, and the residue was partitioned between ethyl acetate and dilute hydrochloric acid. The organic phase was dried and evaporated to give 2,6-dihydro-2-methyl-4-(2-methylpropyl)-1H-pyrrolo[3,4-d]pyridazin-1-one as a red oil (0.65 g).

MS (+ve APCI) 206 ((M+H)$^+$)

$^1$H NMR (CDCl$_3$) δ0.97 (6H, d), 2.08–2.32 (1H, m), 2.62 (2H, m), 3.78 (3H, s), 7.24 (1H, t), 7.57 (1H, t), 11.56 (1H, br).

b) 2,6-Dihydro-2-methyl-4-(2-methylpropyl)-6-phenylmethyl-1H-pyrrolo[3,4-d]pyridazin-1-one A solution of 2,6-dihydro-2-methyl-4-(2-methylpropyl)-1H-pyrrolo[3,4-d]pyridazin-1-one (0.65 g) in dry dimethyl formamide (3 ml) was added dropwise to sodium hydride (0.15 g of a 60% dispersion in oil) in dimethyl formamide (10 ml) with stirring. After 20 minutes benzyl bromide (0.45 ml) and a crystal of potassium iodide were added. The mixture was stirred for 11 days and then poured into dilute hydrochloric acid, which was extracted with ethyl acetate. The organic phase was washed with water, dried, and evaporated to give an oil, which was purified by chromatography on silica (ethyl acetate/isohexane 3:1) to afford, after crystallisation from cyclohexane, 2,6-dihydro-2-methyl-4-(2-methylpropyl)-6-phenylmethyl-1H-pyrrolo[3,4-d]pyridazin-1-one (0.3 g).

Melting point: 104° C.

MS (+ve APCI) 296 ((M+H)+)

$^1$H NMR (CDCl$_3$) δ0.95 (6H, s), 2.12 (1H, m), 2.56 (2H, d), 3.72 (3H, s), 5.27 (2H, s), 7.08 (1H, d(J=2.1 Hz)), 7.16 (2H, m), 7.37 (3H, m), 7.49 (1H, d(J=2.1 Hz)).

EXAMPLE 19

2,6-Dihydro-2-methyl-4-(2-methylpropyl)-6-phenylmethyl-7-(2-pyridinylthio)-1H-pyrrolo[3,4-d]pyridazin-1-one

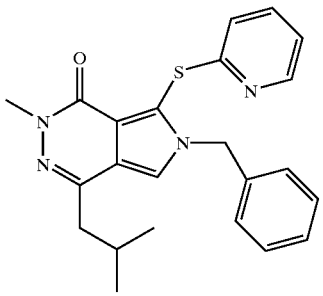

Butyl lithium (2.5M in hexanes, 0.32 ml) was added dropwise to a stirred solution of diisopropylamine (0.11 ml) in dry tetrahydrofuran (2 ml) at 0° C., under nitrogen. The reaction was stirred at 0° C. for 30 minutes, then cooled to −78° C. To this was added a solution of 2,6-dihydro-2-methyl-4-(2-methylpropyl)-6-(1-phenylmethyl)-1H-pyrrolo[3,4-d]pyridazin-1-one (Example 18, 0.2 g) in dry tetrahydrofuran (2 ml), and stirring was continued for 30 minutes. A solution of 2,2'-dipyridyl disulfide (0.155 g) in dry tetrahydrofuran (2 ml) was added. The reaction was allowed to warm to room temperature overnight, and was then quenched by the addition of saturated ammonium chloride solution. The mixture was extracted into diethylether, washed with brine, dried and evaporated to give a yellow oil. Chromatography, eluting with dichloromethane:acetone (4:1), followed by reverse phase HPLC, with an acetonitrile:aqueous ammonium acetate gradient, gave the title compound (0.05 g).

Melting point: 131–132° C.

MS (+ve APCI) ((M+H)$^+$) 405

$^1$H NMR (CDCl$_3$) δ0.97 (d, 6H), 2.06–2.19 (m, 1H), 2.55 (d, 2H), 3.70 (s, 3H), 5.44 (s, 2H), 6.88 (d, 1H), 6.93 (dd, 1H), 7.10–7.12 (m, 2H), 7.25–7.27 (m, 4H), 7.40 (t, 1H), 8.32 (d, 1H).

EXAMPLE 20

2,6-Dihydro-7-[(3-hydroxypropyl)thio]-2-methyl-4-(2-methylpropyl)-6-phenylmethyl-1H-Pyrrolo[3,4-d]pyridazin-1-one

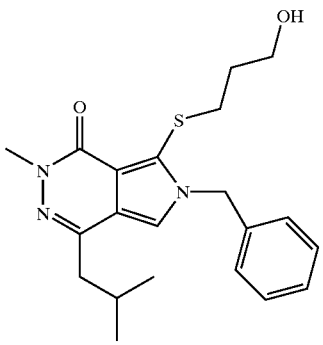

Butyl lithium (2.5M in hexanes, 0.32 ml) was added dropwise to a stirred solution of diisopropylamine (0.11 ml)

in dry tetrahydrofuran (2 ml) at 0° C., under nitrogen. The reaction was stirred at 0° C. for 30 minutes, then cooled to −78° C. To this solution was added a solution of 2,6-dihydro-2-methyl-4-(2-methylpropyl)-6-phenylmethyl-1H-pyrrolo[3,4-d]pyridazin-1-one (Example 18, 0.2 g) in dry tetrahydrofuran (2 ml), and stirring was continued for 30 minutes. A solution of S-[3-{[(1,1-dimethylethyl)dimethylsilyl]oxy}propyl] 4-methylbenzenesulfonothioate, (J. Med. Chem. 1995, 38, 2557., 0.25 g) in dry tetrahydrofuran (2 ml) was added. The reaction was allowed to warm to room temperature overnight, and was then quenched by the addition of saturated ammonium chloride solution. The mixture was extracted into diethylether, washed with brine, dried and evaporated. Chromatography, eluting with ethyl acetate:isohexane (3:7), gave a yellow oil (0.24 g), MS (APCI) 500 (M+H)+.

To a stirred solution of this oil (0.24 g) in methanol (2 ml) was added concentrated hydrochloric acid (0.25 ml). After 2 hours, the reaction was made alkaline by the addition of saturated sodium hydrogen carbonate solution. The mixture was extracted into ethyl acetate, washed with brine, dried and evaporated. Chromatography, eluting with ethyl acetate, followed by trituration with isohexane:diethylether gave the title compound (0.105 g).

Melting point: 91–92° C.

MS (+ve APCI) ((M+H)+) 386

1H NMR (DMSO d-6) δ0.92 (d, 6H), 1.46 (quint, 2H), 2.04–2.14 (m, 1H), 2.53 (d, 2H), 2.88 (t, 2H), 3.30–3.37 (m, 2H), 3.55 (s, 3H), 4.44 (t, 1H), 5.52 (s, 2H), 7.11 (s, 1H), 7.14 (d, 1H), 7.25–7.37 (m, 3H), 7.88 (s, 1H).

EXAMPLE 21

2,6-Dihydro2-methyl-4-(2-methylpropyl)-6-(3,4,5-trimethoxyphenyl)methyl-1H-pyrrolo[3,4-d]pyridazin-1-one

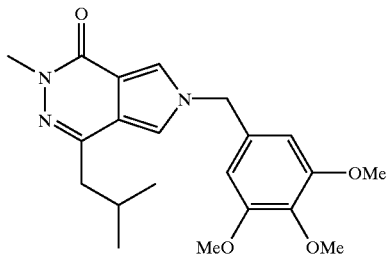

A mixture of 2,6-dihydro-2-methyl-4(2-methylpropyl)-1H-pyrrolo[3,4-d]pyridazin-1-one (Example 18 step a, 0.031 g), 3,4,5-trimethoxybenzyl chloride (0.038 g), and cesium carbonate (0.090 g) in dry dimethyl formamide (0.8 ml) was stirred for 16 hours, and then diluted with dilute hydrochloric acid. The mixture was extracted with ethyl acetate, which was washed with brine, dried, and evaporated to a solid. The solid was purified by chromatography on silica (dichloromethane/ethanol 9:1) to give 2,6-dihydro-2-methyl-4-(2-methylpropyl)-6-[3,4,5-trimethoxyphenyl]methyl-1H-pyrrolo[3,4-d]pyridazin-1-one (0.033 g).

Melting point: 154.5–155°

MS (+ve APCI) 386 ((M+H)+)

1H NMR (CDCl3) δ0.96 (6H, d), 2.14 (1H, m), 2.56 (2H, d), 3.73 (3H, s), 3.81 (6H, s), 3.84 (3H, s), 5.19 (2H, s), 6.37 (2H, s), 7.01 (1H, d(J=2.1 Hz)), 7.50 (1H, d(J=1.8 Hz)).

EXAMPLE 22

2,6-Dihydro-2-methyl-6-(1-naphthalenylmethyl)-4-(1-methylethyl)amino-1H-pyrrolo[3,4-d]pyridazin-1-one

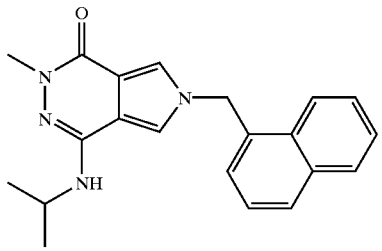

a) Diethyl 1-(1-naphthalenylmethyl)pyrrole-3,4dicarboxylate

Potassium carbonate (5 g) followed by 1-(chloromethyl)naphthalene (4.60 g) were added to a solution of diethyl 3,4-pyrroledicarboxylate (5.00 g) in acetone (50 ml). The mixture was stirred at room temperature for 4 days, dilute hydrochloric acid (100 ml) was added and the mixture was extracted with ether (2×100 ml). The organic extracts were dried, filtered and evaporated to give the sub-title compound as a solid (7.62 g).

1H NMR (CDCl3) δ1.31 (6H, t), 4.27 (4H, q), 5.49 (2H, s), 7.21–7.28 (3H, m), 7.46 (1H, t), 7.50–7.57 (2H, m), 7.80–7.93 (3H, m).

b) 2,3-Dihydro-2-methyl-6-(1-naphthalenylmethyl)-1H-pyrrolo[3,4-d]pyridazin-1,4(6H)-dione Methyl hydrazine (0.55 ml) was added to a solution of diethyl 1-(1-naphthalenylmethyl)pyrrole-3,4-dicarboxylate (1.00 g) in ethanol (10 ml). The mixture was heated at 200° C. in a sealed tube for 3 days. The mixture was evaporated and the residue was purified by column chromatography, eluting with ethyl acetate:methanol (19:1). The resulting solid was suspended in ethyl acetate (25 ml), heated to reflux, and allowed to cool to ambient temperature. The title compound (0.105 g) was collected by filtration.

MS (+ve APCI) 306 ((M+H)+)

1H NMR (DMSO d6) δ3.33 (3H, s), 5.88 (2H, s), 7.32 (1H, d), 7.50–7.64 (5H, m), 7.94 (1H, d), 7.99 (1H, d), 8.19 (1H, d), 10.94 (1H, s, br).

c) 4-Chloro-2,6-dihydro-2-methyl-6-(1-naphthalenylmethyl)-1H-pyrrolo[3,4-d]pyridazin-1-one A suspension of 2,3-dihydro-2-methyl-6-(1-naphthalenylmethyl)-1H-pyrrolo[3,4-d]pyridazine-1,4(6H)-dione (0.10 g) in phosphorus oxychloride (1 ml) was heated at reflux for 30 minutes and then allowed to cool. The solvent was evaporated, water (25 ml) was added and the mixture was extracted with ethyl acetate (2×25 ml). The organic extracts were dried, filtered and evaporated to give the sub-title compound (0.095 g).

MS (+ve APCI) 324/326 ((M+H)+)

d) 2,6-Dihydro-2-methyl-6-(1-naphthalenylmethyl)-4-(2-propyl)amino-1H-pyrrolo[3,4-d]pyridazin-1-one Isopropylamine (1 ml) was added to a solution of 4-chloro-2,6-dihydro-2-methyl-6-(1-naphthalenylmethyl)-

1H-pyrrolo[3,4-d]pyridazine-1-one (0.095 g) in ethanol (4 ml) and the mixture was heated in a sealed tube at 200° C. for 3 days then at 250° C. for 24 hours. The mixture was evaporated and the residue was purified by column chromatography, eluting with ethyl acetate followed by recrystallisation from ethyl acetate/isohexane to give the title compound (0.013 g).

Melting point: 221–222° C. MS (+ve APCI) 347 ((M+H)$^+$)

$^1$H NMR (DMSO d6) δ1.12 (6H, d), 3.39 (3H, s), 3.80–3.92 (1H, m), 5.86 (2H, s), 5.98 (1H, d), 7.34 (1H, d), 7.40 (1H, d), 7.44–7.60 (3H, m), 7.72 (1, d), 7.95–8.01 (2H, m), 8.07–8.10 (1H, m).

EXAMPLE 23

2,6-Dihydro-2-methyl-4-(2-methylpropyl)-6-(4-pyridinyl)methyl-1H-pyrrolo[3,4-d]pyridazin-1-one

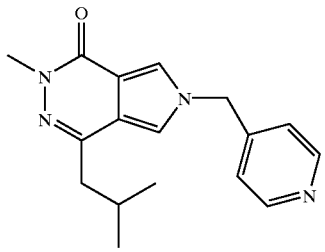

a) 2,6-Dihydro-2-methyl-4-(2-methylpropyl)-1H-pyrrolo[3,4-d]pyridazin-1-one

Methyl 4-(3-methyl-1-oxobutyl)-1H-pyrrole-3-carboxylate (Example 1, step b, 7.8 g) and methylhydrazine (6 ml) were heated at reflux for 18 hours. The solvent was evaporated and the residue was chromatographed, eluting with dichloromethane-ethanol (19:1), to give the sub-title compound as a sand coloured solid (5.2 g).

MS (+ve APCI) ((M+H)$^+$) 206 $^1$H NMR (DMSO d-6) δ0.91 (d, 6H), 2.05–2.18 (m, 1H), 2.54 (d, 2H), 3.54 (s, 3H), 7.46 (t, 1H), 757 (t, 1H), 12.51 (br s, 1H).

b) 2,6-Dihydro-2-methyl-4-(2-methylpropyl)-6-(4-pyridinyl)methyl-1H-pyrrolo[3,4-d]pyridazin-1-one A mixture of 2,6-dihydro-2-methyl(2-methylpropyl)-1H-pyrrolo[3,4-d]pyridazin-1H-one (0.04 g, Example 23, step a), cesium carbonate (0.2 g), 4-chloromethylpyridine hydrochloride (0.035 g) in dimethylformamide (4.5 m) was shaken periodically over 18 hours. The reaction was evaporated at reduced pressure, and the residue was purified by normal phase HPLC, eluting with a dichloromethane:ethanol gradient, to give the title compound (0.024 g).

Melting point: 91–93° C.

MS (+ve APCI) ((M+H)$^+$) 297

$^1$H NMR (CDCl$_3$) δ0.96 (d, 6H), 2.07–2.20 (m, 1H), 2.56 (d, 2H), 3.73 (s, 3H), 5.30 (s, 2H), 6.98–7.01 (m, 3H), 7.51 (d, 1H), 8.61 (d, 2H).

The following examples were prepared and purified following the method of Example 23 step b from 2,6-dihydro-2-methyl-4-(2-methylpropyl)-1H-pyrrolo[3,4-d]pyridazin-1-one, cesium carbonate and the appropriate benzyl halide.

| Example | Name | Melting point ° C. | MS (+ve APCI) ((M + H)$^+$) | $^1$H NMR (CDCl$_3$) δ |
|---|---|---|---|---|
| 24 | 6-(2-Chlorophenyl)-methyl-2,6-dihydro-2-methyl-4-(2-methylpropyl)-1H-pyrrolo[3,4-d]-pyridazin-1-one | 102–104 | 330/332 | 0.97(d, 6H), 2.06–2.19(m, 1H), 2.56(d, 2H), 3.72(s, 3H), 5.38(s, 2H), 6.96(1H, dd), 7.05(1H, d), 7.22–7.34(2H, m) 7.43(1H, dd), 7.49(1H, d) |
| 25 | 6-(3,5-Difluorophenyl)-methyl-2,6-dihydro-2-methyl-4-(2-methylpropyl)-1H-pyrrolo[3,4-d]-pyridazin-1-one | 172–174 | 332 | 0.97(d, 6H), 2.06–2.20(m, 1H), 2.56(d, 2H), 3.73(s, 3H), 5.25(s, 2H), 6.60–6.68(m,2H), 6.79(tt, 1H), 7.00(d, 1H), 7.48(d, 1H) |

-continued

| Example | Name | Melting point ° C. | MS (+ve APCI) ((M + H)+) | ¹H NMR (CDCl₃) δ |
|---|---|---|---|---|
| 26 | 6-(2-Chloro-6-fluorophenyl)methyl-2,6-dihydro-2-methyl-4-(2-methylpropyl)-1H-pyrrolo[3,4-d]-pyridazin-1-one | 124–126 | 348/350 | 0.96(d, 6H), 2.07–2.20(m, 1H), 2.55(d, 2H), 3.70(s, 3H), 5.44(s, 2H), 7.06–7.12(m, 2H), 7.28–7.37(m, 2H), 7.55(d, 1H). |
| 27 | 6-(3-Chloro-2-fluorophenyl)methyl-2,6-dihydro-2-methyl-4-(2-methylpropyl)-1H-pyrrolo[3,4-d]-pyridazin-1-one | 124–127 | 348/350 | 0.96(d, 6H), 2.07–2.20(m, 1H), 2.55(d, 2H), 3.72(s, 3H), 5.33(s, 2H), 6.95(t, 1H), 7.04–7.11(m, 2H), 7.41(t, 1H), 7.50(d, 1H) |
| 28 | 2,6-Dihydro-2-methyl-4-(2-methylpropyl)-6-(2-quinolinylmethyl)-1H-pyrrolo[3,4-d]-pyridazin-1-one | 141–143 | 347 | 0.95(d, 6H), 2.07–2.20(m, 1H), 2.55(d, 2H), 3.73(s, 3H), 5.57(s, 2H), 7.05(d, 1H), 7.14(d, 1H), 7.55–7.63 (m, 2H), 7.74–7.83 (m, 2H), 8.09(d, 1H), 8.13(d, 1H) |
| 29 | 2,6-Dihydro-2-methyl-4-(2-methylpropyl)-6-(2-trifluoromethyl-phenyl)methyl-1H-pyrrolo[3,4-d]-pyridazin-1-one | 127–129 | 364 | 0.96(d, 6H), 2.06–2.20(m, 1H), 2.56(d, 2H), 3.73(s, 3H), 5.49(s, 2H), 6.85(d, 1H), 7.02(d, 1H), 7.42–7.52 (m, 3H), 7.74(d, 1H) |
| 30 | 2,6-Dihydro-6-(2-imidazo[1,2-a]-pyridinyl)methyl-2-methyl-4-(2-methylpropyl)-1H-pyrrolo[3,4-d]-pyridazin-1-one | 165–166 | 336 | 0.96(d, 6H), 2.07–2.21(m, 1H), 2.55(d, 2H), 3.71(s, 3H), 5.43(s, 2H), 6.81(t, 1H), 7.19(d, 1H), 7.22(dd, 1H), 7.43(s, 1H), 7.56–7.60(m, 2H), 8.05(dd, 1H) |

EXAMPLE 31

2,6-Dihydro-N-[3-(1-1H-imidazolyl)propyl]-2methyl-4-(2-methylpropyl)-1-oxo-1-6-phenylmethyl-1H-pyrrolo[3,4-d]pyridazin-1-one-5-carboxamide

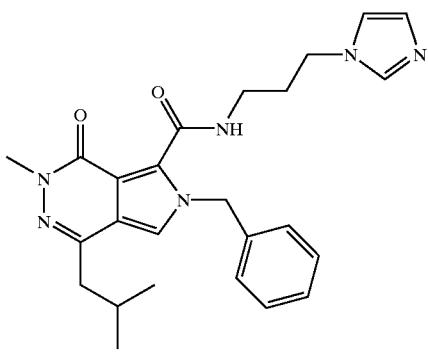

a) 2,6-Dihydro-2-methyl-4-(2-methylpropyl)-6-phenylmethyl-1H-pyrrolo[3,4-d]pyridazin-1-one-5-carboxylic acid Butyl lithium (2.5M in hexanes, 2.35 m) was added dropwise to a stirred solution of diisopropylamine (0.85 ml) in dry tetrahydrofuran (10 ml) at 0° C., under nitrogen. The reaction was stirred at 0° C. for 30 minutes, then cooled to −78° C. To this was added a solution of 2,6-dihydro-2-methyl-4-(2-methylpropyl)-6-(1-phenylmethyl)-1H-pyrrolo[3,4-d]pyridazin-1-one (1.5 g, prepared as in Example 14 step b) in dry tetrahydrofuran (10 ml), and stirring was continued for 30 minutes. This anion was then added to an excess of solid carbon dioxide. The reaction was allowed to warm to room temperature overnight, and was then quenched by the addition of water. The mixture was extracted into ethyl acetate, washed with brine, dried and evaporated to give a yellow oil, which was chromatographed, eluting with ethyl acetate:isohexane(3:7), to give the sub-title compound as a yellow solid (0.91 g).

Melting point: 129–130° C.

MS (+ve APCI) ((M+H)$^+$) 340

$^1$H NMR (CDCl$_3$) δ0.96 (d, 6H), 2.04–2.18 (m, 1H), 2.61 (d, 2H), 3.82 (s, 3H), 5.99 (s, 2H), 7.22–7.38 (m, 6H), 16.43 (s, 1H).

b) 2,6-Dihydro-2-methyl-4-(2-methylpropyl)-6-phenylmethyl-1-pyrrolo[3,4-d]pyridazin-1-one-5-carboxylic acid, 3-(1-imidazolyl)propyl amide A mixture of 2,6-Dihydro-2-methyl-4-(2-methylpropyl)-6-phenylmethyl-1H-pyrrolo[3,4-d]pyridazin-1-one-5-carboxylic acid (0.04 g), hydroxybenzotriazole (0.5 ml, 0.49M in dimethylformamide), 1-(3dimethylaminopropyl)-3-ethylcarbodiimide hydrochloride (0.5 m, 0.47M in dimethylformamide) and N-(3-aminopropyl)imidazole (0.03 g) in dimethylformamide (3 ml) were shaken periodically over 48 hours. The solvent was evaporated, and the residue was chromatographed, eluting with dichloromethane:ethanol (19:1) to give the title compound (0.011 g).

MS (+ve APCI) ((M+H)$^+$) 447

$^1$H NMR (CDCl$_3$) δ0.98 (d, 6H), 2.12–2.20 (m, 3H), 2.62 (d, 2H), 3.40 (q, 2H), 3.82 (s, 3H), 4.15 (q, 2H), 6.05 (s, 2H), 7.10 (d, 2H), 7.20 (s, 1H), 7.30–7.40 (m, 5H), 8.61 (s, 1H), 11.81 (t, 1H).

EXAMPLE 32

2,5-Dihydro-5-methyl-7-(2-methylpropyl)-2-(1-naphthalenylmethyl)-4H-pyrazolo[3,4-d]pyridazin-4-one

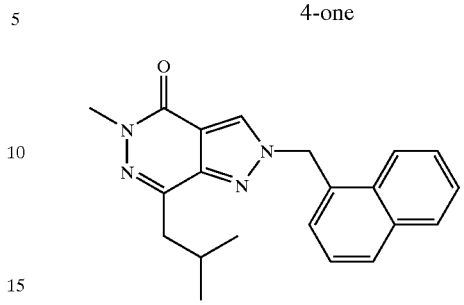

a) Ethyl 4-hydroxy-6-methyl-2-heptynoate n-Butyl lithium (2.5M in hexanes, 22.5 ml) was added dropwise over 40 minutes with stirring to fresh ethyl propiolate (6.0 ml) in dry tetrahydrofuran (75 ml) under nitrogen, with the temperature being maintained below −68° by external cooling. After 30 minutes, isovaleraldehyde (6.5 ml) in dry tetrahydrofuran (15 ml) was added over 15 minutes with the temperature maintained below −69°. After one hour, trimethylsilyl chloride (10 ml) was added and the reaction was allowed to warm to room temperature. Water was added and the mixture was extracted with ethyl acetate, which was washed with brine, dried, and evaporated to give ethyl 4hydroxy-6-methyl-2-heptynoate as an oil (9.5 g).

GC/MS (after BSTMA) EI: 241 (M−15)

b) Ethyl 6-methyl-4-oxo-2-heptynoate

Jones' reagent (from chromium trioxide, 4 g) was added dropwise with stirring to ethyl 4-hydroxy-6-methyl-2-heptynoate (9.5 g) in acetone (30 ml) in an ice bath, with the temperature being maintained at about 10°. After 0.5 hour the reaction was diluted with water (300 ml) and extracted with diethyl ether thrice. The organic phase was washed with brine, dried, and evaporated to give ethyl 6-methyl-4-oxo-2-heptynoate as an oil (7.0 g).

GC/MS EI: 167 (M−15)

$^1$H NMR (CDCl$_3$) δ0.97 (6H, d), 1.30 (3H, t), 2.20 (1H, m), 2.51 (2H, d), 4.30 (2H, q).

c) Ethyl 5-(3-methyl-1-oxobutyl)-1H-pyrazole-4-carboxylate, and ethyl 4-(3-methyl-1-oxobutyl)-1H-pyrazole-5-carboxylate (Trimethylsilyl)diazomethane (2.0M in hexanes, 25 ml) was added slowly with stirring under nitrogen to ethyl 6-methyl-4-oxo-2-heptynoate (7.0 g) in drytetrahydrofuran (20 ml) in a cold water bath. After 16 hours the reaction was evaporated to an oil, which was subjected to chromatography on silica (ethyl acetate/isohexane 1:2) to give the first eluted product, ethyl 5-(3-methyl-1-oxobutyl)-1H-pyrazole4-carboxylate (2.33 g).

Melting point: 105–107° C.

MS (+ve APCI) 225 ((M+H)$^+$)

$^1$H NMR (CDCl$_3$) δ0.99 (6H, d), 1.38 (3H, t), 2.25 (1H, m), 3.07 (2H, d), 4.35 (2H,q), 8.12 (1H, s), 11.5 (1H,br).

The second eluted product was ethyl 4(3-methyl-1-oxobutyl)-1H-pyrazole-5-carboxylate (1.22 g).

Melting point: 61–62° C.

MS (+ve APCI) 226 ((M+H)+)

¹H NMR (CDCl₃) δ0.98 (6H, d), 1.42 (3H, t), 2.23 (1H, m), 2.79 (2H, d), 4.46 (2H,q), 8.09 (1H, s), 12.55 (1H, br).

d) Ethyl 3-(3-methyl-1-oxobutyl)-1-(1-naphthalenylmethyl)-1H-pyrazole-4-carboxylate Ethyl 5-(3-methyl-1-oxobutyl)-1H-pyrazole4-carboxylate (0.75 g), 1-naphthalenemethyl chloride (0.6 g), and cesium carbonate (1.25 g) in dry dimethyl formamide (15 ml) were stirred under nitrogen for 24 hours, and then dilute hydrochloric acid was added. The mixture was extracted with ethyl acetate, which was washed with brine, dried, and evaporated to give the sub-title compound as a gum.

MS AP+ve 365 (M+1)

¹H NMR (CDCl₃) δ0.98 (6H, d), 1.26 (3H, t), 2.21–2.37 (1H, m), 2.92 (2H, d), 4.21 (2H, q), 5.77 (2H, s), 7.39–7.57 (2H, m), 7.50 (1H, d), 7.61 (1H, s), 7.80–7.95 (2H, m), 7.95 (1H, d).

e) 2,5-Dihydro-5-methyl-7-(2-methylpropyl)-2-(1-naphthalenylmethyl)-4H-pyrazolo[3,4-d]pyridazin-4-one Ethyl 3-(3-methyl-1-oxobutyl)-1-(1-naphthalenylmethyl)-1H-pyrazole-4-carboxylate (1.8 g) and methylhydrazine (0.6 ml) in ethanol (20 ml) were heated underreflux for 16 hours. The solution was cooled and evaporated to a solid, which was purified by chromatography on silica (ethyl acetate:isohexane 2:3) followed by crystallisation from ethyl acetate/cyclohexane to give 2,5-dihydro-5-methyl-7-(2-methylpropyl)-2-(1-naphthalenylmethyl)-4H-pyrazolo[3,4-d]pyridazin-4-one (0.43 g).

Melting point 166–167°

MS (+ve APCI) 347 ((M+H)⁺)

¹H NMR (CDCl₃) δ1.02 (6H, d), 2.38 (1H, m), 2.82 (2H, d), 3.71 (3H, s), 5.97 (2H, s), 7.35–7.50 (4H, m), 7.86 (1H, s), 7.86 (1H, d), 7.91 (1H, d), 7.93 (1H, d).

EXAMPLE 33

2,6-Dihydro-6-methyl-4-(2-methylpropyl)-2-(1-naphthalenylmethyl)-7H-pyrazolo[3,4-d]pyridazin-7-one

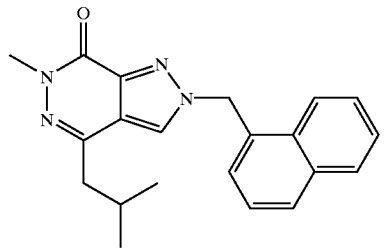

a) Ethyl 4-(3-methyl-1-oxobutyl)-1-(1-naphthalenylmethyl)-1H-pyrazole-3-carboxylate Ethyl 4-(3-methyl-1-oxobutyl)-1H-pyrazole-5-carboxylate (Example 32, step c; 0.62 g), 1-naphthalenylmethyl chloride (0.53 g), and cesium carbonate (1.1 g) were stirred in dry dimethylformamide (8 ml) for 48 hours, and then dilute hydrochloric acid was added. The mixture was extracted with ethyl acetate, which was washed with brine, dried, and evaporated to give ethyl 4-(3-methyl-1-oxobutyl)-1-(1-naphthalenylmethyl)-1H-pyrazole-3-carboxylate as a gum. (0.15 g)

MS (+ve APCI) 365 ((M+H)⁺)

¹H NMR (CDCl₃) δ0.87 (6H, d), 1.43 (3H, t), 2.12 (1H, m), 2.66 (2H, d), 4.47 (2H, q), 5.80 (2H, s), 7.50 (1H, s), 7.4–7.6 (4H, m), 7.8–7.9 (3H, m)

b) 2,6-Dihydro-6-methyl-4-(2-methylpropyl)-2-(1-naphthalenylmethyl)-7H-pyrazolo[3,4-d]pyridazin-7-one A mixture of ethyl 4-(3-methyl-1-oxobutyl)-1-(1-naphthalenylmethyl)-1H-pyrazole-3-carboxylate (0.15 g) and methylhydrazine (0.1 ml) in ethanol (2 ml) was heated at reflux for 18 hours. The reaction was diluted with water and then extracted into ethyl acetate. The organic phase was washed with brine, dried, filtered and evaporated. The residue was chromatographed, eluting with dichloromethane:ethanol (19:1), to give the title compound (0.08 g).

Melting point 163–164° C.

MS (+ve APCI) ((M+H)⁺) 347

¹H NMR (CDCl₃) δ0.85 (d, 6H), 1.89–2.03 (m, 1H), 2.44 (d, 2H), 3.80 (s, 3H), 6.03 (s, 2H), 7.46–7.55 (m, 5H), 7.90–7.96 (m, 3H).

EXAMPLE 34

2,5-Dihydro-3-[(3-hydroxypropyl)thio]-5-methyl-7-(2-methylpropyl)-2-(1-naphthalenylmethyl)-4H-pyrazolo[3,4-d]pyridazin-4-one

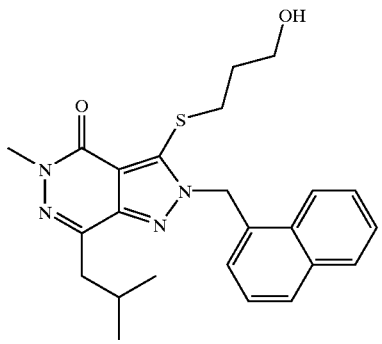

Lithium diisopropylamide (0.4M in tetrahydrofuran, 2.0 ml) was added slowly to a solution of 2,5-dihydro-5-methyl-7-(2-methylpropyl)-2-(1-naphthalenylmethyl)-4H-pyrazolo[3,4d]pyridazin-4-one (0.17 g) and S-[3-{[(1,1-dimethylethyl)-dimethylsilyl]oxy}propyl]4methyl-benzenesulfonothioate, (J. Med. Chem. 1995, 38, 2557., 0.34 g) in dry tetrahydrofuran (7 ml) stirred at −78° under nitrogen. After 3 hours saturated sodium hydrogen carbonate solution was added, and the mixture was allowed to 15 warm to ambient temperature and then extracted with ethyl acetate. The organic phase was washed with brine, dried, and evaporated to an oil (0.4 g). The oil was dissolved in acetonitrile (7 ml) and treated with hydrofluoric acid (40%, 0.4 ml). After 16 hours an excess of sodium hydrogen carbonate solution was added, and the mixture was extracted with ethyl acetate, which was then washed with brine, dried, and evaporated. The residue was purified by chromatography on silica (ethyl acetate:isohexane 2:1) to give a solid which was crystallised from cyclohexane/ethyl acetate to afford 2,5-dihydro-3-[(3-hydroxypropyl)thio]-5-methyl-7-

(2-methylpropyl)-2-(1-naphthalenylmethyl)-4H-pyrazolo[3,4-d]pyridazin-4-one (0.135 g).

Melting point 141–142° C.

MS (+ve APCI) 437 ((M+H)+)

¹H NMR (CDCl₃) δ0.97 (6H, d), 1.76 (2H, quint), 2.30 (1H, m), 2.76 (2H, d), 3.27 (2H, t), 3.43 (1H, t), 3.76 (3H, s), 3.80 (2H, q), 6.18 (2H, s), 6.88 (1H, d), 7.3–7.6 (3H, m), 7.81 (1H, d), 7.90 (1H, d), 8.27 (1H, d).

EXAMPLE 35

2-[1-Hydroxy-1-(1-naphthalenyl)methyl]-5-methyl-7-(2-methylpropyl)furan[2,3-d]pyridazin-4(5H)one

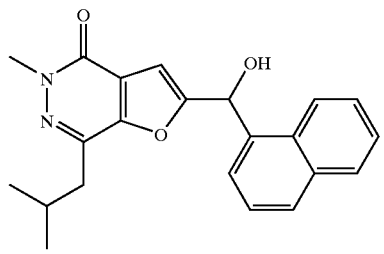

a) 2-(1-Hydroxy-3-methylbutyl)furan-3-carboxylic acid

3-Furoic acid (2.85 g) was dissolved in tetrahydrofuran (50 ml) and cooled to −78° C. A solution of lithium diisopropylamide (56 mmol) in tetrahydrofuran (100 ml) was added dropwise and the mixture was stirred for 15 minutes. A solution of 3-methylbutanal (3.0 ml) in tetrahydrofuran (15 ml) was added dropwise. The reaction mixture was stirred at −78° C. for 1 h and then allowed to warm to ambient temperature. The mixture was poured into water, the aqueous phase was acidified with 2M hydrochloric acid and the mixture was extracted twice with ethyl acetate. The organic phases were washed with brine, dried, filtered and evaporated. Chromatography, eluting with dichloromethane:ethyl acetate:acetic acid (160:40:1), gave the sub-title compound (2.75 g).

MS (−ve APCI) 197 ((M−H)−)

¹H NMR (CDCl₃) δ0.96 (6H, m), 1.62–1.89 (3H, m), 5.12 (1H, dd), 6.73 (1H, d), 7.32 (1H, d).

b) Trimethylsilylmethyl ²-(1-hydroxy-3-methylbutyl)furan-3-carboxylate 2-(1-Hydroxy-3-methylbutyl)furan-3carboxylic acid (800 mg) was dissolved in dichloromethane (30 ml) an d a solution of trimethysilyldiazomethane (2M in hexane, 2.1 ml) was added. The mixture was stirred for 20 h, then diluted with dichloromethane and washed twice with hydrochloric acid. The organic phase was washed with brine, then dried, filtered and evaporated. Chromatography, eluting with diethylether:isohexane (1:1), gave the sub-title compound (435 mg).

MS (+ve APCI) 267 ((M−Me)+)

¹H NMR (CDCl₃) δ0.12 (9H, s), 0.95 (6H, dd), 1.60–1.88 (3H, m), 3.96 (2H, s), 4.37 (1H, d), 5.01 (1H, m), 6.64 (1H, d), 7.26 (1H, d).

c) Trimethylsilylmethyl 2-(3-methyl-1-oxobutyl)furan-3-carboxylate

Dimethylsulfoxide (125 μl) was dissolved in dichloromethane (10 ml) and cooled to −78° C. Oxalyl chloride (80 μl) was added dropwise and the mixture was stirred for 15 minutes. Trimethylsilylmethyl 2-(1-hydroxy-3-methylbutyl)furan-3-carboxylate (200 mg) in dichloromethane (10 ml) was added and the mixture was stirred for 20 minutes. Triethylamine (0.49 ml) was added. The mixture was stirred for 20 minutes, and then allowed to warm to ambient temperature. The mixture was poured onto water and then extracted thrice with ethyl acetate. The organic phases were combined, washed with brine, dried, filtered and evaporated to give the sub-title compound (170 mg).

MS (+ve APCI) 283 ((M+H)+)

d) 5-Methyl-7-(2-methylpropyl)furo[2,3-dpyridazin-4(5H)-one

Trimethylsilylmethyl 2-(3-methyl-1-oxobutyl)furan-3-carboxylate (170 mg) and methyl hydrazine (4 μl) were combined in xylene (10 ml) and the mixture was heated under reflux for 5 hours. The mixture was allowed to cool to ambient temperature, poured onto water and then extracted twice with ethyl acetate. The combined organic phases were washed with brine, dried, filtered and evaporated. Chromatography, eluting with isohexane:ethyl acetate (3:2), gave the sub-title compound (49 mg).

MS (+ve APCI) 207 ((M+H)+)

¹H NMR (CDCl₃) δ0.98 (6H, d), 2.12–2.26 (1H, d), 2.73 (2H, d), 3.84 (3H, s), 7.05 (1H, d), 7.65 (1H, d).

e) 2-[1-Hydroxy-1-(1-naphthalenyl)methyl]-5-methyl-7-(2-methylpropyl)furo[2,3-d]pyridazin-4(5H)-one 5-Methyl-7-(2-methylpropyl)furo[2,3-dpyridazin-4(5H)-one (105 mg) was dissolved in tetrahydrofuran (5 ml) and cooled to −78° C. Lithium diisopropylamide in tetrahydrofuran (1M, 0.56 ml) was added to the solution and the mixture was stirred for 30 minutes. 1-Naphthaldehyde (8 μl) was added and the reaction was stirred for 30 minutes, and then allowed to warm to ambient temperature. The mixture was poured onto water and extracted thrice with ethyl acetate. The combined organic phases were washed with brine, dried, filtered and evaporated. Chromatography, eluting with isohexane:ethyl acetate (1:1), gave the title compound (50 mg).

Melting point 110–112° C.

MS (+ve APCI) 363 ((M+H)+)

¹H NMR (CDCl₃) δ0.91 (6H, dd), 2.04–2.18 (1H, m), 2.67 (2H, d), 2.81 (1H, d), 3.79 (3H, s), 6.66 (1H, d), 6.73,(1H, s), 7.48–7.53 (3H, m), 7.65 (1H, d), 7.87–7.91 (2H, m), 8.04–8.06 (1H, m).

EXAMPLE 36

5-Methyl-7-(2-methylpropyl)2-(1-naphthalenyl)methyl)furo]-2,3-d]pyridazin-4(5H)one

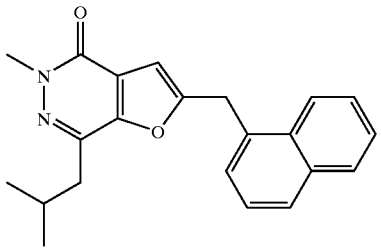

2-[1-Hydroxy-1-(1-naphthalenyl)methyl]-5-7-(2-methylpropyl)furo[2,3-d]pyridazin-4(5H)one (68 mg) was dissolved in dichloromethane (3 ml). Trifluoroacetic acid (1 ml) and triethylsilane (1 ml) were added and the mixture was stirred for 24 hours. The mixture was poured onto 2M sodium hydroxide solution and was then extracted twice with ethyl acetate. The combined organic phases were washed with brine, dried, filtered and evaporated. Chromatography, eluting with isohexane:ethyl acetate (1:1), gave the title compound (52 mg).

Melting point 73–75° C.

MS (+ve APCI) 347 ((M+H)$^+$)

$^1$H NMR (CDCl$_3$) δ0.94 (6H, d), 2.08–2.22 (1H, m), 2.69 (2H, d), 3.79 (3H, s), 4.56 (2H, s), 6.50 (1H, s), 7.37–7.53 (4H, m), 7.81–7.99 (3H, m).

EXAMPLE 37

2-[1-Hydroxy-1-(3-cyanophenyl)methyl]-5-methyl-7-(2-methylpropyl)furo[2,3-d]pyridazin-4(5H)one

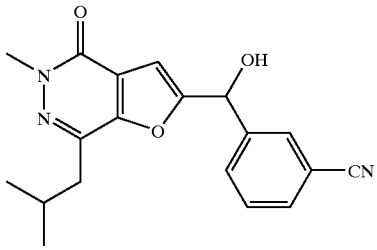

Prepared from 5-methyl-7-(2-methylpropyl)furo[2,3-d]pyridazin-4(5H)-one (example 35 step d) and 3-cyanobenzaldehyde following the method of Example 35 step e.

Melting point: 106–108° C.

MS (+ve APCI) 338 ((M+H)$^+$)

$^1$H NMR (CDCl$_3$) δ0.93 (6H, d), 2.04–2.18 (1H, m), 2.67 (2H, d), 3.30 (1H, d), 3.81 (3H, s), 6.00 (1H, d), 6.81 (1H, s), 7.52 (1H, t), 7.67 (2H, m), 7.81 (1H, s).

EXAMPLE 38

2-(3-Cyanophenyl)methyl-5-methyl-7-(2methylpropyl)furo[2,3-d]pyridazin-4(5H)one

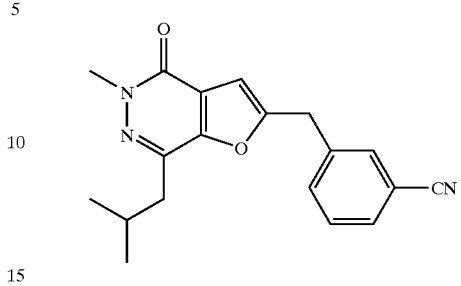

Prepared from 2-[1-hydroxy-1-(3-cyanophenyl)methyl]-5-methyl-7-(2-methylpropyl)furo[2,3-d]pyridazin-4(5H)one following the method of Example 36.

Melting point: 76–78° C.

MS (+ve APCI) 322 ((M+H)$^+$)

$^1$H NMR (CDCl$_3$) δ0.95 (6H, d), 2.13 (1H, m), 3.68 (2H, d), 3.82 (3H, s), 4.17 (2H, s), 6.68 (1H, s), 7.44–7.52 (2H, m), 7.58–7.60 (2H, m).

EXAMPLE 39

2-(2-Trifluoromethylphenyl)methyl-5-methyl-7-(2-methylpropyl)thieno[2,3-d]pyridazin-4(5H)-one

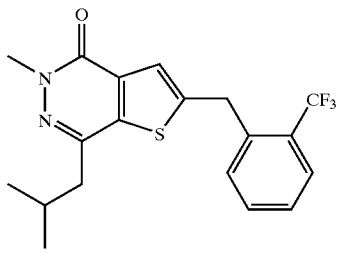

A solution of lithium diisopropylamide (11.3 mmol) in tetrahydrofuran/hexane (2:1, 16 ml) was added dropwise to a solution of 5-methyl-7-(2-methylpropyl)thieno[2,3-d]pyridazin-4(5H)-one (Example 6 step b, 1.00 g) in tetrahydrofuran (20 ml) at −78° C. under nitrogen. After 5 minutes, 2-trifluoromethylbenzaldehyde (1.57 g) was added. The mixture was stirred at −78° C. for 3 hours, then saturated sodium hydrogen carbonate solution (50 ml) was added, and the mixture was warmed to room temperature and extracted with ethyl acetate (50 ml). The organic extracts were washed twice with saturated sodium hydrogen carbonate solution, then with brine, then dried, filtered and evaporated. The residue was dissolved in trifluoroacetic acid (5 ml) and triethylsilane (2 ml) was added. After 24 hours, additional trifluoroacetic acid (5 ml) and triethylsilane (2 ml) were added. After a further 3 days, the mixture was diluted with water (50 ml) and extracted with ethyl acetate (50 ml). The organic extracts were washed twice with 1M sodium hydroxide solution, then with brine, and then dried, filtered and evaporated. The residue was purified by column chromatography, eluting with an ethyl acetate/isohexane gradient, followed by preparative normal-phase HPLC with gradient dichloromethane/ethanol elution and then with gradient ethyl acetate/isohexane elution to give the title compound (0.055 g).

Melting point 112–114° C.

MS (+ve APCI) 381 ((M+H)$^+$)

¹H NMR (CDCl₃) δ0.97 (6H, d), 2.12–2.24 (1H, m), 2.59 (2H, d), 3.81 (3H, s), 4.41 (2H, s), 7.35–7.43 (3H, m), 7.53 (1H, t), 7.70 (1H, d).

EXAMPLE 40

2-[(1-Hydroxy-1-pyridin-3-yl)methyl]-5-methyl-7-(2-methylpropyl)thieno[2,3-d]pyridazin-4(5H)-one hydrochloride

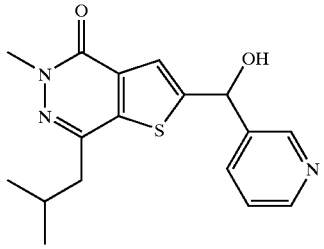

Reaction of 5-methyl-7-(2-methylpropyl)thieno[2,3-d]pyridazin-4(5H)-one (Example 6 step b 1.00 g) and 3-pyridinecarboxaldehyde (0.96 g) according to the procedure of example 14 gave the crude title compound as the free base. This material was purified by column chromatography, eluting with an ethyl acetate/ethanol gradient, then dissolved in ether (50 ml) and treated with 4M hydrogen chloride in 1,4-dioxane (0.5 ml). The precipitated solid was collected and dried in vacuo to give the title compound (0.06 g).

Melting point: 154–156° C.

MS (+ve APCI) 330 ((M+H)⁺)

¹H NMR (DMSO d6) δ0.96 (6H, d), 1.39 (1H, s), 2.10–2.24 (1H, m), 2.59 (2H, d), 3.80 (3H, s), 6.16 (1H, s), 7.32 (1H, dd), 7.43 (1H, s), 7.81 (1H, dt), 8.55 (1H, dd), 8.68 (1H, d).

EXAMPLE 41

5-Methyl-7-(2-methylpropyl)-2-(3-pyridinylmethyl)thieno[2,3-d]pyridazin-4(5H)-one

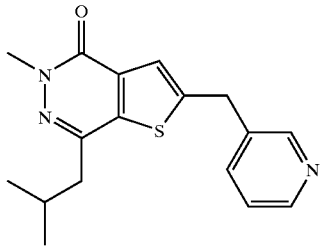

Prepared from 2-[(1-hydroxy-1-pyridin-3-yl)methyl]-5-methyl-7-(2-methylpropyl)thieno[2,3-d]pyridazin-4(5H)-one hydrochloride (example 40, 0.54 g) according to the procedure for Example 43b. The crude product was purified by column chromatography, eluting with ethyl acetate-:methanol:aqueous ammonia solution (99:0:1, 94:5:1 then 89:10:1) followed by trituration with ether to give the title compound (0.30 g).

Melting point: 118–119° C.

MS (+ve APCI) 314 ((M+H)⁺)

¹H NMR (CDCl₃) δ0.96 (6H, d), 2.13–2.22 (1H, m), 2.59 (2H, d), 3.81 (3H, s), 4.25 (2H, s), 7.28 (1H, dd), 7.43 (1H, s), 7.57 (1H, d), 8.54–8.57 (2H, m).

EXAMPLE 42

2-(2-Chloro-6-fluorophenyl)methyl-5-methyl-7-(2-methylpropyl)thieno[2,3-d]pyridazin-4(5H)-one

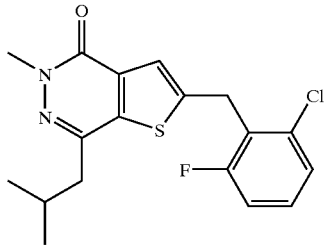

Prepared from 5-methyl-7-(2-methylpropyl)thieno[2,3d]pyridazin-4(5H)one (example 6 step b 1.00 g) and 2chloro-6-fluorobenzaldehyde (0.96 g) according to the is procedure of Example 14. The crude product was purified by preparative normal-phase HPLC with gradient dichloromethane/ethanol elution followed by recrystallisation from isohexane to give the title compound (0.07 g).

Melting point 85–86° C.

MS (+ve APCI) 365/367 ((M+H)⁺)

¹H NMR (CDCl₃ ) δ0.97 (6H, d), 2.15–2.24 (1H, m), 2.59 (2H, d), 3.80 (3H, s), 4.39–4.40 (2H, s), 7.01–7.08 (1H, m), 7.19–7.26 (2H, m), 7.42 (1H, s).

EXAMPLE 43

2-[(1-Hydroxy-1-quinolin-3-yl)methyl]-5-methyl-7-(2-methylpropyl)thieno[2,3-d]pyridazin-4(5H)-one

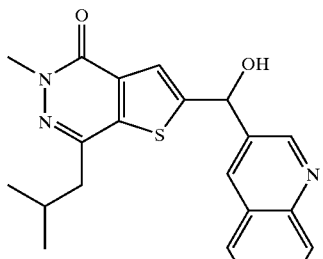

Prepared from 5-methyl-7-(2-methylpropyl)thieno[2,3-d]pyridazin-4(5H)-one (example 6 step b, 1.00 g) and 3quinolinecarboxaldehyde (1.06 g) according to the procedure of example 14. The crude product was purified column chromatography, eluting with ethyl acetate:triethylamine (99:1) then ethyl acetate/methanol/triethylamine (89:10:1) to give the tide compound (0.50 g) as an oil.

MS (+ve APCI) 380 ((M+H)⁺).

EXAMPLE 44

5-Methyl-7-(2-methylpropyl-2-(3-guinolinylmethyl)thieno[2,3-d]pyridazin-4(5H)-one hydrochloride

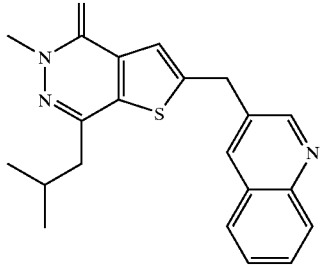

Thionyl chloride (0.10 ml) was added to a solution of 2-[(1-hydroxy-1-quinolin-3-yl)methyl]-5-methyl-7-(2-methylpropyl)thieno[2,3-d]pyridazin-4(5H)-one in dichloromethane (8 ml) at room temperature. After 3 hours, the solution was evaporated. The residue was dissolved in ethyl acetate (15 ml). Triethylamine (0.50 ml) was added and the solution was hydrogenated over palladium on carbon (5%, 0.035 g) for 20 hours. The mixture was filtered, and the catalyst was washed with ethyl acetate (50 ml). The filtrate was washed with water, then twice with saturated sodium hydrogen carbonate solution, and then with brine. The organic phase was dried, filtered and evaporated. The residue was purified by column chromatography, eluting with ethyl acetate:isohexane:triethylamine (50:50:1, 66:33:1 then 100:0:1). The resulting oil was dissolved in ether (50 ml) and treated with 4M hydrogen chloride in 1,4-dioxane (0.5 ml). The precipitated solid was collected and dried in vacuo to give the title compound (0.09 g).

Melting point >230° C. (dec)

MS (+ve APCI) 364 ((M+H)$^+$)

$^1$H NMR (DMSO d6) δ0.90 (6H, d), 2.06–2.15 (1H, m), 2.58 (2H, d), 3.68 (3H, s), 4.66 (2H, d), 7.60 (1H, s), 7.78 (1H, t), 7.95 (1H, t), 8.14–8.20 (2H, m), 8.74 (1H, s), 9.18 (1H, s).

EXAMPLE 45

2-(3-Chlorophenyl)methyl-3-(2-hydroxyethoxy)-7-(methoxymethyl)-5-methylthieno[2,3-d]pyridazin-4(5H)-one

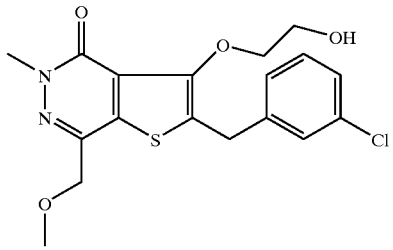

a) Methyl 5-[(3-chlorophenyl)methyl]-4-hydroxythiophene-3-carboxylate

Methyl 4-oxotetrahydrothiophene-3-carboxylate (18.5 g) and 3-chlorobenzaldehyde (48.5 g) were heated at 100° C. with piperidine (4 ml) for 15 minutes and then allowed to cool to room temperature. The resulting yellow solid was stirred in methanol (300 ml) for 18 hours and collected. The yellow solid was suspended in ethanol (300 m) and dichloromethane (200 ml), para-toluenesulfonic acid(10 g) was added and the suspension was heated at reflux for 48 hours. The reaction mixture was allowed to cool and was then concentrated. The residue was purified by chromatography, eluting with 10:1 isohexane:dichloromethane, to give the sub-title compound (22.32 g).

MS (+ve APCI) ((M+H)$^+$) 283/5

$^1$H NMR (DMSO d-6) δ3.79 (3H, s), 4.08 (2H, s), 7.04 (1H, s), 7.33–7.39 (1H, m), 7.45–7.57 (2H, m), 7.65 (1H, s), 10.76 (1H, s).

b) Methyl 5-[(3-chlorophenyl)methyl]4-{2-[(1,1-dimethylethyl)dimethylsilyl]oxyethoxy}thiophene-3-carboxylate A mixture of methyl 5-[(3chlorophenyl)methyl]-4-hydroxythiophene-3-carboxylate (11 g), potassium carbonate (5.45 g) and (2-bromoethoxy)(1,1-dimethylethyl)dimethylsilane (10 g) was dissolved in acetone (250 m) and heated at reflux for 36 hours and then allowed to cool. The mixture was filtered, concentrated and purified by chromatography, eluting with 10:1 ethyl acetate:isohexane, to give the sub-title compound (8 g).

MS (+ve APCI) ((M+H)$^+$) 442/4 c) 5-[(3-Chlorophenyl)methyl]4-{2-[(1,1-dimethylethyl)dimethylsilyl]oxyethoxy}thiophene-3-carboxylic acid Methyl 5-[(3-chlorophenyl)methyl]-4-{2-[(1,1-dimethylethyl)dimethylsilyl]oxyethoxy}thiophene-3-carboxylate (10.2 g) was dissolved in a mixture of 1M lithium hydroxide (50 ml), methanol (50 ml) and tetrahydrofuran (150 ml) and stirred for 18 hr. The reaction mixture was concentrated and the residue was partitioned between dichloromethane and 2M hydrochloric acid. The organic layer was collected, dried and filtered. t-Butyl-dimethylsilyl chloride (7 g) and imidazole (3.1 g) were added to the solution and the mixture was stirred for 72 hours. The reaction mixture was concentrated and the residue was dissolved in methanol. Potassium carbonate (5 g) was added to the solution and the suspension was vigorously stirred for 3 minutes, then filtered and concentrated. The residue was dissolved in ethyl acetate, washed with 2M hydrochloric acid, dried, filtered and concentrated. The residue was purified by chromatography, eluting with 10:1:1 isohexane-:ethyl acetate:acetic acid, to give the sub-title compound (4.2 g).

MS (−ve APCI) ((M−Me)$^−$) 427/9 d) 2-[(3-Chlorophenyl)methyl]-3-(2-hydroxyethoxy)-7-(methoxymethyl)-5-methylthieno[2,3-d]pyridazin-4(5H)-one 2.0M butyl lithium in hexanes (1 ml) was diluted with tetrahydrofuran (3 ml) and cooled to −20° C. 5-[(3-Chlorophenyl)methyl]-4-{2-[(1,1-dimethylethyl)-dimethylsilyl]oxyethoxy}thiophene-3carboxylic acid in tetrahydrofuran (1 ml of 1M solution) was added slowly. The solution was mixed for 10 minutes and then 1 mmol of 2,N-Dimethoxy-N-methylacetamide in 1 ml of tetrahydrofuran was added. The solution was mixed for 10 minutes and was then added to 5 m of ammonium chloride solution. The reaction mixture was evaporated in air for 18 hours. The residue was dissolved in dichloromethane and washed with water twice. The solvent was allowed to evaporate and the residue was then dissolved in 5 ml of ethanol. To this solution was added 92 mg of methyl hydrazine. The resulting solution was heated at reflux for 4 hours. The reaction mixture was allowed to cool and the solvent was evaporated. Purification by column chromatography, eluting with an isohexane:ethyl acetate gradient, gave the title compound (4 mg).

MS(+ve APCI) 395/397 (M+H)

$^1$H NMR (DMSO d-6) δ3.33 (3H, s), 3.76 (3H, s), 3.80–3.84 (2H, br), 4.12 (2H, s), 4.134.16 (2H, m), 4.48 (2H, s), 7.07–7.98 (4H, m).

The following compounds were made following the method of Example 44 using the appropriate N,O-dimethylhydroxylamide.

| Example | Name | MS(+ve APCI) ((M + H)+) | 1H NMR (DMSO d-6) δ |
|---|---|---|---|
| 46 | 2-[(3-Chlorophenyl)methyl]-7-cyclohexyl-3-(2-hydroxyethoxy)-5-methylthieno[2,3-d]pyridazin-4(5H)-one | 433/435 | 1.19–1.88(10H, m), 2.52–2.62(1H, m), 3.74(3H, s), 3.82(2H, bs), 4.11(2H, s), 4.14–4.17(2H, m), 7.06–7.09(4H, m) |
| 47 | 2-[(3-Chlorophenyl)methyl]-3-(2-hydroxyethoxy)-5-methyl-7-phenylthieno[2,3-d]pyridazin-4(5H)-one | 427/429 | 3.86(3H, s), 2.82–2.86(2H, m), 4.13(2H, s), 4.18–4.21(2H, m), 7.14–7.17(2H, m), 7.40–7.43(4H, m), 7.67–7.71(3H, m) |
| 48 | 2-[(3-Chlorophenyl)methyl]-7-cyclopentyl-3-(2-hydroxyethoxy)-5-methylthieno[2,3-d]pyridazin-4(5H)-one | 419/421 | 0.76–0.86(4H, m), 1.73–1.86(5H, m), 3.74(3H, s), 3.02–3.13(2H, m), 4.11(2H, s), 4.13–4.18(2H, m), 7.06–7.11(4H, m) |

EXAMPLE 49

7-Cyclopropylmethyl-3-methoxy-5-methyl-2-[(3-trifluoromethylphenyl)methyl]thieno[2,3-d]pyridazin-4(5H)-one

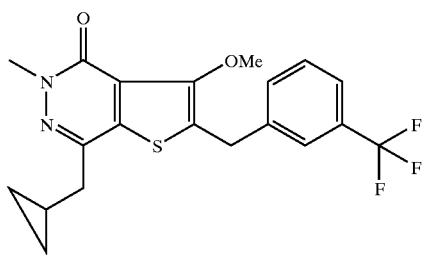

a) Butyl 5-[(3-trifluoromethylphenyl)methyl]-4-hydroxythiophene-3-carboxylate

Methyl 4-oxotetrahydrothiophene-3-carboxylate (3.2 g) and 3-trifluoromethyl-benzaldehyde (10.6 g) were heated at 100° C. with piperidine (170 mg) for 15 minutes and then allowed to cool to room temperature. The resulting yellow solid was stirred in 150 ml methanol for 18 hours and then collected. The yellow solid was suspended in butanol (150 ml) with para-toluenesulfonic acid (10 g) and heated at reflux for 48 hours. The reaction mixture was concentrated and chromatographed, eluting with 10:1 isohexane:dichloromethane, to give the sub-title compound (2.5 g).

MS (+ve APCI) ((M+H)+) 359 b) Butyl 4-methoxy-2-[(3-trifluoromethylphenyl)methyl]-thiophene-3-carboxylate

Butyl 5-[(3-trifluoromethylphenyl)methyl]-4-hydroxythiophene-3-carboxylate (2.5 g) was dissolved in acetone (50 ml). Potassium carbonate (1 g) and methyl iodide (0.454 ml) were added and the mixture was heated at reflux for 18 hours. The reaction mixture was allowed to cool and then concentrated. The residue was dissolved in ethyl acetate, washed with water, dried, filtered and evaporated. The residue was purified by chromatography, eluting with 40:1 isohexane:ethyl acetate, to give the sub-title compound (1.75 g).

1H NMR (DMSO d-6) δ0.92 (3H, t), 1.34–1.47 (2H, m), 1.61–1.70 (2H, m), 3.72 (3H, s), 4.18 (2H, s), 4.21 (2H, d), 7.55–7.62 (4H, m), 8.10 (1H, s).

c) 4-Methoxy-5-[(3-trifluoromethylphenyl)methyl]thiophene-3-carboxylic acid

Butyl 4-methoxy-2-[(3-trifluoromethylphenyl)methyl]thiophene-3-carboxylate (1.75 g) was dissolved in a mixture of 1M lithium hydroxide (10 ml), tetrahydrofuran (30 ml) and methanol (10 ml) and the solution was stirred for 18 hours. The reaction mixture was concentrated. The residue was redissolved in ethyl acetate and then washed 2M hydrochloric acid. The organic layer was dried and concentrated to give the sub-title compound as a white solid (1.25 g).

MS (−ve APCI) ((M−H)⁻) 315

¹H NMR (DMSO d-6) δ3.71 (3H, s), 4.16 (2H, s), 7.54–7.61 (4H, m), 8.04 (1H, s), 12.64 (1H, s).

d) 2-(2-Cyclopropylacetyl)-4-methoxy-5-[(3-trifluoromethylphenyl)methyl]thiophene-3-carboxylic acid 2M butyl lithium in hexanes (1.75 ml) was added slowly to a solution of 4-methoxy-5-[(3-trifluoromethylphenyl)methyl]thiophene-3-carboxylic acid (500 mg) in tetrahydrofuran (30 ml) at −78° C. The resultant red solution was stirred for 20 minutes and then 2-cyclopropyl-N-methoxy-N-methylacetamide (229 mg) in tetrahydrofuran (3 ml) was added. The mixture was stirred for 20 minutes at −78° C. and was then allowed to warm to room temperature. After 5 hours water was added and the mixture was extracted with ethyl acetate. The organic phase was dried and concentrated. Purification of the residue by chromatography, eluting with 10:10:1 isohexane:ether:acetic acid, gave the sub-title compound (177 mg).

MS (+ve APCI) ((M+H)⁺) 399

¹H NMR (DMSO d-6) δ0.91–1.14 (2H, m), 0.44–0.49 (2H, m), 0.94–1.14 (1H, m), 2.66 (2H, d), 3.77 (3H, s), 4.26 (2H, s), 7.56–7.66 (3H, m), 7.69 (1H, s), 13.66 (1H, bs).

e) 7-Cyclopropylmethyl-3-methoxy-5-methyl-2-[(3-trifluoromethylphenyl)methyl]thieno[2,3d]pyridazin-4(5H)-one 2-(2-Cyclopropylacetyl)-4-methoxy-5-[(3-trifluoromethylphenyl)methyl]thiophene-3-carboxylic acid (8.65 g) was dissolved in 125 ml of ethanol. To this solution was added methylhydrazine (2.34 ml) and the mixture was heated at reflux for 18 hours. The reaction mixture was allowed to cool and then concentrated. The residue was partitioned between ethyl acetate and 2M hydrochloric acid The organic layer was collected, dried, filtered and concentrated to give the title compound (8.8 g).

MS (+ve APCI) ((M+H)⁺) 409

¹H NMR (DMSO d-6) δ0.22(2H, m), 0.48(2H, m), 1.00–1.10 (1H, m), 2.61(2H, d), 3.69(3H, s), 3.88(3H, s), 4.33(2H, s), 7.55–7.64(3H, m), 7.69(1H, s).

EXAMPLE 50

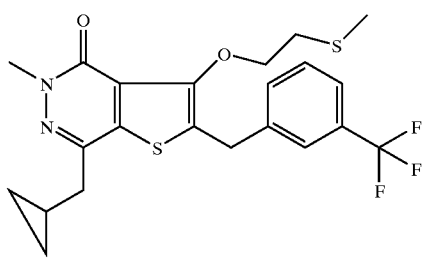

7-Cyclopropylmethyl-5-methyl-3-[2-(methylthio)ethoxy]-2-[(3-trifluoromethylphenyl)methyl]thieno[2,3-d]pyridazin-4(5H)-one a) 7-Cyclopropylmethyl-3-hydroxy-5-methyl-2-[(3-trifluoromethylphenyl)methyl]thieno[2,3-d]pyridazin-4(5H)-one 7-Cyclopropylmethyl-3-methoxy-5-methyl-2-[(3-trifluoromethylphenyl)methyl]-thieno[2,3-d]pyridazin-4(5H)-one (8.8 g) was dissolved in dichloromethane (250 ml) and cooled to −15° C. Boron tribromide in dichloromethane (1M, 24 ml) was added. The reaction was allowed to warm to room temperature and left to stir for 72 hours. Water was added and the mixture was extracted with ethyl acetate. The ethyl acetate was dried, filtered and concentrated. The residue was purified by chromatography, eluting with 1:1 isohexane:ether, and then recrystallised from isohexane to give the sub-title compound (4.5 g).

Melting point 92–93° C.

MS (+ve APCI) ((M+H)⁺) 395

¹H NMR (DMSO d-6) δ0.21–0.23 (2H, m), 0.48–0.50 (2H, m), 1.04–1.08 (1H, m), 2.60 (2H, d), 3.67 (3H, s), 4.26 (2H, s), 7.56–7.64 (3H, m), 7.67 (1H, s), 9.27 (1H, s).

b) 7-Cyclopropylmethyl-5-methyl-3-[2-(methylthio)ethoxy]-2-[(3-trifluoromethylphenyl)methyl]thieno[2,3-d]pyridazin-4(5H)-one To 5 ml of dry tetrahydrofuran was added 0.64 ml of 1M triphenylphosphine in tetrahydrofuran followed by 0.64 ml of 1M diethyl diazodicarboxylate in tetrahydrofuran and then by 0.64 ml of 1M 2,6-di-t-butylphenol in tetrahydrofuran. This mixture was mixed for 5 minutes and then 1.28 ml of 0.5M 2-(methylthio)ethanol in tetrahydrofuran was added. The solution was then mixed for 5 minutes. 7-Cyclopropylmethyl-3-hydroxy-5-methyl-2-[(3-trifluoromethylphenyl)methyl]thieno[2,3-d]pyridazin-4(5H)-one (248 mg in 1 ml tetrahydrofuran) was added and the solution was mixed periodically over 24 hours. The solution was opened to the air for 18 hours and then purified by chromatography, eluting with an isohexane ethyl acetate gradient, to give the title compound (77 mg).

MS (ES+ve, TOF) ((M+H)⁺) found: 469.1241; theory: 469.1231

¹H NMR (DMSO d-6) δ0.21–0.23 (2H, m), 0.48-0/50 (2H, m), 1.02–1.08 (1H, m), 2.11 (3H, s), 2.66 (2H, d), 2.85 (2H, t), 3.69 (3H, s), 4.30 (2H, t), 4.40 (2H, s), 7.56–7.64 (3H, m), 7.72 (1H, s).

The following examples were prepared following the method of Example 50 using the appropriate alcohol as reactant.

| Example | Name | MS(ES + ve, TOF) ((M + H)+) | 1H NMR (DMSO d-6) δ |
|---|---|---|---|
| 51 | 7-Cyclopropyl-methyl-3-(2-methoxyethoxy)-5-methyl-2-[(3-trifluoromethyl-phenyl)methyl]-thieno[2,3-d]-pyridazin-4(5H)-one. | found: 453.1442 theory: 453.1459 | 0.21–0.23(2H, m), 0.47–0.49(2H, m), 1.01–1.05(1H, m), 2.61(2H, d), 3.30(3H, s), 3.59–3.62(2H, m), 3.68(3H, s), 4.31–4.32(2H, m), 4.36(2H, s), 7.55–7.63(3H, m), 7.71(1H, s) |
| 52 | 3-Cyclopentyl-methoxy-7-cyclopropylmethyl-5-methyl-2[(3-trifluoromethyl-phenyl)methyl]-thieno[2,3-d]-pyridazin-4(5H)-one. | found: 477.1835 theory: 477.1823 | 0.21–0.24(2H, m), 0.47–0.50(2H, m), 1.02–1.04(1H, m), 1.33–1.35(2H, m), 1.53–1.55(4H, m), 1.73–1.77(2H, m), 2.31–2.33(1H, m), 2.61(2H, d), 3.68(3H, s), 3.97(2H, d), 4.34(2H, s), 7.55–7.63(3H, m), 7.69(1H, s) |
| 53 | 7-Cyclopropylmethyl-5-methyl-3-(tetrahydrofuran-2-ylmethoxy)-2-[(3-trifluoromethyl-phenyl)methyl]-thieno[2,3-d]-pyridazin-4(5H)-one | found: 479.1701 theory: 479.1616 | 0.22–0.26(2H, m), 0.45–0.49(2H, m), 1.01–1.03(H, m), 1.60–1.70(1H, m), 1.80–1.90(2H, m), 1.91–1.99(1H, m), 2.60(2H, d), 3.45(3H, s), 3.60–3.70(1H, m), 3.70–3.79(1H, m), 4.01–4.09(1H, m), 4.11–4.19(1H, m), 4.18–4.26(1H, m), 4.37(2H, d), 7.55–7.65(3H, m), 7.71(1H, s) |
| 54 | 7-Cyclopropylmethyl-3-(3-hydroxy-3-methyl-butoxy)-5-methyl-2-[(3-trifluoromethyl-phenyl)methyl]-thieno[2,3-d]-pyridazin-4(5H)-one | found: 481.1762 theory: 481.1772 | 0.21–0.23(2H, m), 0.47–0.49(2H, m), 1.02–1.06(1H, m), 1.06(6H, s), 1.86(2H, t), 2.62(2H, d), 3.68(3H, s), 4.20(2H, t), 4.32(1H, s), 4.33(2H, s), 7.53–7.57(3H, m), 7.68(1H, s) |

-continued

| Example | Name | MS(ES + ve, TOF) ((M + H)+) | 1H NMR (DMSO d-6) δ |
|---|---|---|---|
| 55 | N-{3-[7-Cyclopropylmethyl-5-methyl-4-oxo-2-[(3-trifluoromethyl-phenyl)methyl]-4,5-dihydrothieno-[2,3-d]pyridazin-3-yl]oxypropyl}-acetamide. | found: 494.1731 theory: 494.1725 | 0.19–0.21(2H, m), 0.46–0.48(2H, m), 1.02–1.04(1H, m), 1.80(3H, s), 1.85–1.89(2H, m), 2.63(2H, d), 3.23–3.27(2H, m), 3.69(3H, s), 4.09(2H, t), 4.34(2H, s), 6.34(1H, s), 7.57–7.63(3H, m), 7.95(1H, s) |
| 56 | 7-Cyclopropylmethyl-3-([1,3]dioxolan-4-ylmethoxy)-5-methyl-2-[(3-trifluoromethyl-phenyl)methyl]-thieno[2,3-d]-pyridazin-4(5H)-one | found: 481.1416 theory: 481.1409 | 0.19–0.21(2H, m), 0.45–0.47(2H, m), 1.04–1.08(1H, m), 2.61(2H, d), 3.67(3H, d), 3.74–4.25(2H, dm), 4.01(2H, d), 4.36–4.42(2H, d), 4.56(1H, t), 4.79–4.99(2H, dm), 7.57–7.64(3H, m), 7.71–7.85(1H, m) |
| 57 | 7-Cyclopropylmethyl-5-methyl-3-(4-oxopentyl)oxy-2-[(3-trifluoromethyl-phenyl)methyl]-thieno[2,3-d]-pyridazin-4(5H)-one | found: 479.1631 theory: 479.1616 | 0.23–0.27(2H, m), 0.52–0.56(2H, m), 1.07–1.11(1H, m), 2.09–2.11(2H, m), 2.19(3H, s), 2.63(2H, d), 2.76(2H, t), 3.81(3H, s), 4.17(2H, t), 4.22(2H, s), 7.42–7.44(2H, m), 7.51–7.53(2H, m) |

Pharmacological Data
Inhibition of Human Mixed Lymphocyte Reaction (MLR)

The MLR test was performed in 96-well flat bottomed microtitre plates. Compounds were prepared as 10 mM stock solution in dimethyl sulfoxide. A 50 fold dilution of this was prepared in a RPMI 1640 medium cell culture solution. Serial dilutions were prepared from this solution. 10 µl of the 50 fold diluted stock, or dilutions of it, were added to the wells to give concentrations in the assay starting at 9.5 µm and decreasing. Into each well was placed $1.5 \times 10^5$ cells from each of two responding donors in a final volume of 0.2 ml RPMI 1640 medium supplemented with 10% human serum, 2 mM L-glutamine and penicillin/streptomycin. The cells were incubated at 37° C. in a humidified atmosphere at 5% carbon dioxide for 120 hours. $^3$H-Thymidine (0.5 µCi) was added for the final 6 hours of the incubation. The level of radioactivity incorporated by the cells was then determined, which is a measure of T-cell proliferation.

The title compounds of Examples 1 to 57 were found to exhibit an $IA_{50}$ value of less than $1 \times 10^{-6}$M in the above test.

What is claimed is:

1. A compound of the formula

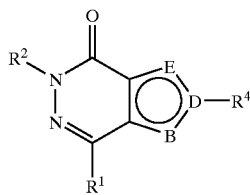

(I)

wherein B represents a nitrogen (N) atom; D represents a nitrogen (N) atom; E represents a group $CR^3$;

$R^1$ represents a group NR'R" where R' represent a hydrogen atom or a $C_1$–$C_6$ alkyl group, R" represents a $C_1$–$C_6$ alkyl group, or R' and R" together with the nitrogen atom to which they are attached form a 3- to 7-membered saturated heterocyclic ring, or $R^1$ represents a $C_1$–$C_6$ alkyl, $C_1$–$C_6$ alkoxy, $C_1$–$C_3$-alkyloxy$C_1$–$C_3$-alkyl, $C_3$–$C_6$-cycloalkyloxy$C_1$–$C_3$-alkyl, $C_3$–$C_6$ alkenyl, phenyl, $C_3$–$C_7$ cycloalkyl, $C_3$–$C_5$ cycloalkylmethyl or $C_3$–$C_7$ cycloalkenyl group, each of which is optionally substituted by one or more halogen atoms; $R^2$ represents a methyl group, or a $C_1$–$C_6$ alkyl group optionally substituted by a $C_1$–$C_6$ alkoxy group other than in the 1-position; $R^3$ represents a hydrogen atom or a group X-$R^5$ or X-$Ar^1$; X represents a group —O—, S(O)$_n$, SO$_2$N($R^6$); C(=O)N($R^6$); n is 0, 1 or 2;

$R^5$ represents an optionally substituted alkyl or alkenyl group, or, additionally, in the case where X represents SO$_2$N($R_6$) or C(=O)N($R^6$), $R^5$ and $R^6$ together with the nitrogen atom to which they are attached may form an optionally substituted 3- to 7-membered heterocyclic ring; $Ar^1$ represents an optionally substituted phenyl or pyridyl group;

represents a hydrogen atom, $C_1$–$C_6$ alkyl or is linked to $R^5$ as defined above; $R^4$ represents a group $CHR^7Ar^2$ or $Ar^3$ $Ar^2$ represents an aryl or heteroaryl group which is optionally substituted; $Ar^3$ represents an acenaphthenyl, indanyl or fluorenyl group, each of which is optionally substituted; and $R^7$ represents a hydrogen atom or a $C_1$–$C_4$ alkyl group; or a pharmaceutically-acceptable salt or solvate thereof.

2. A compound according to claim 1, wherein $R^1$ represents a $C_1$–$C_4$ alkylamino group, or $R^1$ represents a $C_3$–$C_5$ alkyl, $C_1$–$C_4$ alkoxy, $C_1$–$C_3$ -alkyloxy $C_1$–$C_3$ -alkyl, $C_3$–$C_6$ -cycloalkyloxy $C_1$–$C_3$ -alkyl, $C_3$–$C_6$ alkenyl, phenyl, $C_3$–$C_5$ cycloalkyl, $C_3$–$C_5$ cycloalkylmethyl or $C_3$–$C_6$ cycloalkenyl group, each of which is optionally substituted by one to four halogen atoms.

3. A compound according to claim 1, wherein $R^2$ represents a methyl group, or a $C_2$–$C_6$ alkyl group optionally substituted by a $C_1$–$C_4$ alkoxy group other than in the 1-position.

4. A compound according to claims 1 wherein $R^4$ represents a group $CHR^7Ar^2$, $C(O)Ar^2$ or $CR^7(OH)Ar^2$.

5. A compound according to claim 4, wherein $Ar^2$ represents a phenyl, naphthyl, pyridyl, quinolinyl, isoquinolinyl, naphthyridinyl, cinnolinyl, phthalazinyl, quinazolinyl, quinoxalinyl, thienyl, benzothienyl, furanyl, benzofuranyl, thiazolyl, benzothiazolyl, indolyl, indolizinyl, pyrazolyl, indazyl, imidazolyl, benzimidazolyl, imidazopyridyl, triazolyl, benzotriazolyl or triazolopyridyl group, each of which is optionally substituted by one or more substituent groups independently selected from halogen, trifluoromethyl, trifluoromethoxy, amino, cyano, carboxyl, nitro, $C_1$–$C_6$ alkyl, $C_1$–$C_6$ alkoxy, (di)$C_1$–$C_6$ alkylamino, $C_2$–$C_6$ acylamino, $C_1$–$C_6$ alkylsulfonamido, CONH-($C_1$–$C_6$ alkyl) and $C_1$–$C_6$ alkoxycarbonyl.

6. A compound according to any claim 1, wherein X represents a group —O—, S(O)$_n$ where n is 0, 1 or 2, or a group C(=O)N($R^6$).

7. A compound according claim 1 wherein $R^5$ represents a $C_2$–$C_6$ alkyl or $C_2$–$C_6$ alkenyl group optionally substituted by one or more substituent groups independently selected from amido, amino, carboxyl, cyano, hydroxyl, $C_1$–$C_6$ alkoxy, $C_1$–$C_6$ alkylthio, $C_1$–$C_6$ alkylcarbonyl, $C_1$–$C_6$ alkoxycarbonyl, $C_3$–$C_7$ cycloalkyl, (di) $C_1$–$C_6$ alkylamino, $C_2$–$C_6$ acylamino, $C_1$–$C_6$ alkylsulfonamido, tetrahydrofuranyl, dioxolanyl, imidazolyl, halo$C_1$–$C_6$ alkylsulfonamido and tetrazolyl.

8. A compound according to claim 1, wherein $Ar^1$ represents a phenyl or pyridyl group optionally substituted by one or more substituent groups independently selected from carboxyl, hydroxyl, $C_2$–$C_6$ acylamino, $C_1$–$C_6$ alkylamido, $C_1$–$C_6$ alkylsulfonamido and (di)$C_1$–$C_6$ alkylsulfamoyl.

9. A compound according to claim 1 being: 2,5-Dihydro-5-methyl-7-(2-methylpropyl)-2-(1-naphthalenylmethyl)-4H-pyrazolo[3,4-d]pyridazin-4-one, 2,5-Dihydro-3-[(3-hydoxypropyl)thio]-5-methyl-7-(2-methylpropyl)-2-(1-naphthalenylmethyl)-4H-pyrazolo[3,4-d]pyridazin-4-one.

10. A pharmaceutical composition comprising a compound of formula (I), or a pharmaceutically-acceptable salt or solvate thereof, as claimed in claim 1 in association with a pharmaceutically-acceptable adjuvant, diluent or carrier.

11. A process for the preparation of a pharmaceutical composition which comprises mixing a compound of formula (I), or a pharmaceutically-acceptable salt or solvate thereof, as defined in claim 1 with a pharmaceutically-acceptable adjuvant, diluent or carrier.

12. A method of treating allograft rejection in a patient in need of such treatment, said method comprising administering to said patient a therapeutically effective amount of a compound of formula (I), or a pharmaceutically-acceptable salt or solvate thereof, as claimed in claim 1.

13. A method of treating rheumatoid arthritis in a patient in need of such treatment, said method comprising administering to said patient a therapeutically effective amount of a compound of formula (I), or a pharmaceutically-acceptable salt or solvate thereof, as claimed in claim 1.

* * * * *